(12) United States Patent
Kim

(10) Patent No.: US 10,709,397 B2
(45) Date of Patent: Jul. 14, 2020

(54) MOBILE X-RAY APPARATUS

(71) Applicant: SAMSUNG ELECTRONICS CO., LTD., Suwon-si (KR)

(72) Inventor: Myeong-je Kim, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 16/441,202

(22) Filed: Jun. 14, 2019

(65) Prior Publication Data

US 2019/0290229 A1    Sep. 26, 2019

Related U.S. Application Data

(63) Continuation of application No. 15/471,657, filed on Mar. 28, 2017, now Pat. No. 10,321,883.

(30) Foreign Application Priority Data

Jan. 11, 2017    (KR) .................. 10-2017-0004164

(51) Int. Cl.
*A61B 6/00* (2006.01)
*A61B 6/10* (2006.01)
(Continued)

(52) U.S. Cl.
CPC .......... *A61B 6/4405* (2013.01); *A61B 5/7405* (2013.01); *A61B 6/10* (2013.01); *A61B 6/4411* (2013.01); *A61B 6/56* (2013.01); *G01R 31/50* (2020.01); *G01T 1/175* (2013.01); *H01M 10/052* (2013.01); *H02H 7/18* (2013.01); *H02J 7/007* (2013.01); *H02J 7/0021* (2013.01);
(Continued)

(58) Field of Classification Search
None
See application file for complete search history.

(56) References Cited

U.S. PATENT DOCUMENTS 5,808,376 A   9/1998  Gordon et al.
7,022,290 B2  4/2006  Gural et al.
(Continued)

FOREIGN PATENT DOCUMENTS

EP    2865333 A1    4/2015
JP    200264947 A   2/2002
(Continued)

OTHER PUBLICATIONS

Communication dated Mar. 9, 2018 from the European Patent Office in counterpart application No. 17182962.5.
(Continued)

*Primary Examiner* — Hoon K Song
(74) *Attorney, Agent, or Firm* — Sughrue Mion, PLLC

(57) ABSTRACT

A mobile X-ray apparatus includes: an X-ray radiation device; a controller configured to control the X-ray radiation device; a power supply configured to supply operating power to the X-ray radiation device and the controller via a lithium ion battery and control overcurrent occurring during X-ray emission by the X-ray radiation device; and a charger configured to charge the power supply. Each of the controller, the power supply, and the charger is embodied in a physically separate module, and each of the power supply and the charger is encased in a metal case.

9 Claims, 22 Drawing Sheets

(51) Int. Cl.
  *G01T 1/175* (2006.01)
  *H02J 7/00* (2006.01)
  *H02J 7/02* (2016.01)
  *H02H 7/18* (2006.01)
  *H05G 1/12* (2006.01)
  *A61B 5/00* (2006.01)
  *G01R 31/50* (2020.01)
  *H01M 10/052* (2010.01)
  *H02H 3/08* (2006.01)
  *G01R 31/36* (2020.01)
  *H01M 10/0525* (2010.01)
  *H01M 10/48* (2006.01)
  *H01M 10/42* (2006.01)

(52) U.S. Cl.
  CPC .......... *H02J 7/0029* (2013.01); *H02J 7/0031* (2013.01); *H02J 7/0068* (2013.01); *H02J 7/0077* (2013.01); *H02J 7/02* (2013.01); *H02J 7/025* (2013.01); *H05G 1/12* (2013.01); *A61B 2560/0214* (2013.01); *G01R 31/3648* (2013.01); *H01M 10/0525* (2013.01); *H01M 10/4257* (2013.01); *H01M 10/486* (2013.01); *H02H 3/08* (2013.01); *H02J 7/00304* (2020.01)

(56) References Cited

U.S. PATENT DOCUMENTS

| | | |
|---|---|---|
| 7,864,923 B2 | 1/2011 | Ohta et al. |
| 8,030,898 B2 | 10/2011 | Okuto |
| 8,963,499 B2 | 2/2015 | Choi |
| 9,490,460 B2 | 11/2016 | Yanagi |
| 9,655,582 B2 | 5/2017 | Shirota et al. |
| 2005/0117706 A1 | 6/2005 | Powell |
| 2008/0278116 A1 | 11/2008 | Matsunaga |
| 2009/0184679 A1 | 7/2009 | Yeh |
| 2009/0190718 A1 | 7/2009 | Fan |
| 2011/0110498 A1 | 5/2011 | Takae et al. |
| 2011/0123001 A1 | 5/2011 | Kopcienski et al. |
| 2011/0163701 A1* | 7/2011 | Carrier ............... H01M 2/1022 318/139 |
| 2011/0317817 A1 | 12/2011 | Nishino et al. |
| 2012/0163543 A1 | 6/2012 | Fuse et al. |
| 2012/0256099 A1 | 10/2012 | Gregerson et al. |
| 2012/0268066 A1 | 10/2012 | Endo et al. |
| 2013/0127418 A1 | 5/2013 | Oh et al. |
| 2013/0223596 A1 | 8/2013 | Kojima et al. |
| 2014/0167704 A1 | 6/2014 | Lafontaine et al. |
| 2014/0173300 A1 | 6/2014 | Yamazaki et al. |
| 2014/0369477 A1 | 12/2014 | Okuno |
| 2015/0015168 A1 | 1/2015 | Terao |
| 2015/0318720 A1 | 11/2015 | Aradachi et al. |
| 2016/0089985 A1 | 3/2016 | Murayama et al. |
| 2016/0296187 A1* | 10/2016 | Neumann ................ H05G 1/32 |
| 2016/0315487 A1 | 10/2016 | Shim |
| 2017/0027537 A1* | 2/2017 | Zhang ..................... H05G 1/12 |
| 2017/0086776 A1 | 3/2017 | Kim |

FOREIGN PATENT DOCUMENTS

| | | |
|---|---|---|
| JP | 2005-147822 A | 6/2005 |
| JP | 2007267559 A | 10/2007 |
| JP | 2010273827 A | 12/2010 |
| JP | 201342643 A | 2/2013 |
| JP | 20143846 A | 1/2014 |
| JP | 2015-118773 A | 6/2015 |
| KR | 10-2001-0008484 A | 2/2001 |
| KR | 101075037 B1 | 10/2011 |
| KR | 1020120037682 A | 4/2012 |
| KR | 10-2014-0060801 A | 5/2014 |
| KR | 1020150047749 A | 5/2015 |
| KR | 10-2016-0125852 A | 11/2016 |
| WO | WO2011063637 A1 * | 6/2011 |
| WO | 2015/158180 A1 | 10/2015 |
| WO | 2016/050202 A1 | 4/2016 |

OTHER PUBLICATIONS

Communication dated Oct. 16, 2017 by the Korean Intellectual Property Office in counterpart Korean Patent Application No. 10-2017-0004164.

Communication dated Aug. 4, 2017, issued by the European Patent Office in counterpart European Application No. 16207528.7.

Communication dated Aug. 17, 2017, issued by the Korean Intellectual Property Office in counterpart Korean Application No. 10-2016-0099133.

* cited by examiner

MOBILE X-RAY APPARATUS

CROSS-REFERENCE TO RELATED APPLICATION

This is a continuation application of U.S. patent application Ser. No. 15/471,657, filed Mar. 28, 2017, in the U.S. Patent and Trademark Office, which claims priority from Korean Patent Application No. 10-2017-0004164, filed Jan. 11, 2017, in the Korean Intellectual Property Office. The disclosure of the above-named application is incorporated herein by reference in its entirety.

BACKGROUND

1. Field

The present disclosure relates to X-ray apparatuses including lithium ion batteries.

2. Description of the Related Art

X-rays are electromagnetic waves having wavelengths of 0.01 to 100 angstroms (Å), and are widely used, due to their ability to penetrate objects, in medical apparatuses for imaging the inside of a living body or in non-destructive testing equipment for industrial use.

An X-ray apparatus using X-rays may obtain X-ray images of an object by transmitting X-rays emitted from an X-ray source through an object and detecting a difference in intensities of the transmitted X-rays via an X-ray detector. The X-ray images may be used to examine an internal structure of an object and diagnose a disease of the object. The X-ray apparatus facilitates observation of an internal structure of an object by using a principle in which penetrating power of an X-ray varies depending on the density of the object and atomic numbers of atoms constituting the object. As a wavelength of an X-ray decreases, penetrating power of the X-ray increases and an image on a screen becomes brighter.

Since an X-ray radiation device and an X-ray detector of the X-ray apparatus are generally affixed to a specific space, a patient needs to be transferred to an examination room where the X-ray apparatus is located for X-ray imaging.

However, it is difficult to use a general X-ray apparatus in the case of performing X-ray imaging examinations on patients with mobility problems. Thus, a mobile X-ray apparatus has been developed to perform X-ray imaging without space limitations.

In the mobile X-ray apparatus, an X-ray radiation device is mounted on a movable main body, and a portable X-ray detector is used. Due to this configuration, the mobile X-ray apparatus may be taken directly to a patient with reduced mobility in order to perform X-ray imaging.

Lead-acid batteries are generally inexpensive and are widely used in mobile X-ray apparatuses.

However, lead-acid batteries have a short life span (two years or 500 cycles), are bulky and heavy, and may release hazardous materials into the environment.

Furthermore, use of such bulky or heavy lead-acid batteries is inconvenient when trying to move an X-ray apparatus.

SUMMARY

Provided are mobile X-ray apparatuses including lithium ion batteries that have a relatively long life span, are small and lightweight, and are environmentally-friendly as they do not release hazardous materials, compared to lead-acid batteries.

Additional aspects will be set forth in part in the description which follows and, in part, will be apparent from the description, or may be learned by practice of the presented embodiments.

According to an aspect of an embodiment, a mobile X-ray apparatus includes: an X-ray radiation device; a controller configured to control the X-ray radiation device; a power supply configured to supply operating power to the X-ray radiation device and the controller via a lithium ion battery and control overcurrent occurring during X-ray emission by the X-ray radiation device; and a charger configured to charge the power supply, wherein the controller, the power supply, and the charger are each constituted by a physically separate module, and the power supply and the charger are each encased in a metal case.

The power supply may include: the lithium ion battery; a battery management system (BMS) circuit configured to detect a state of the lithium ion battery and control an operation of the power supply; a discharge field effect transistor (FET) configured to control the overcurrent and including a plurality of FETs connected in parallel; and a charge FET.

The discharge FET and the charge FET are further configured to control a path of a discharge current or a charge current when the lithium ion battery is discharged or charged.

The BMS circuit is further configured to control an operation of a protection circuit protecting against at least one of over-discharge, overcurrent, overheating, and unbalancing between cells in the lithium ion battery.

The power supply may further include a first current sensor and a second current sensor, and the BMS circuit is further configured to detect, during the X-ray emission by the X-ray radiation device, the overcurrent by activating the second current sensor.

The mobile X-ray apparatus may further include a current sensor located at an output terminal of the charger in order to detect a charge current.

The controller, the power supply, and the charger may respectively include communication connectors, and the controller, the power supply, and the charger are configured to communicate with one another via the communication connectors according to a controller area network (CAN) protocol.

The power supply may include a temperature sensor configured to detect a temperature of the lithium ion battery, and the controller is further configured to directly monitor information about the temperature detected by the temperature sensor.

The power supply and the charger may respectively include interrupt pins that can be directly controlled by the controller, and the controller is further configured to respectively turn off the power supply and the charger via the interrupt pins.

The power supply is further configured to receive data necessary to update firmware for the BMS circuit from the controller via the communication connector.

The power supply is further configured to receive, when the power supply is connected to the controller via the communication connector, data necessary to update firmware for the BMS circuit, from the controller.

The BMS circuit may include a master BMS circuit and a plurality of slave BMS circuits, and each of the slave BMS circuits may be directly connected to the lithium ion battery to detect information about the state of the lithium ion battery and transmit the detected information to the master BMS circuit via a communication interface.

The lithium ion battery may include a plurality of cell groups, each cell group having a plurality of lithium ion battery cells connected in parallel.

A battery pack may be formed by connecting the plurality of cell groups of the lithium ion battery in series, and the battery pack may be connected to each of the slave BMS circuits.

The lithium ion battery may include four lithium ion battery cells that are connected in parallel to form a cell group.

The metal case of the power supply may include at least one handle.

A weight of the power supply may be less than or equal to 35 kilograms (kg).

A partition wall may be provided between the lithium ion battery and the BMS circuit.

Each cell in the lithium ion battery may be inserted into a holder made of a flame retardant material.

The mobile X-ray apparatus may further include a frame that is attached to a main body of the mobile X-ray apparatus via a hinge so as to be capable of pivoting around a hinge axis, and a system board may be mounted on the frame.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
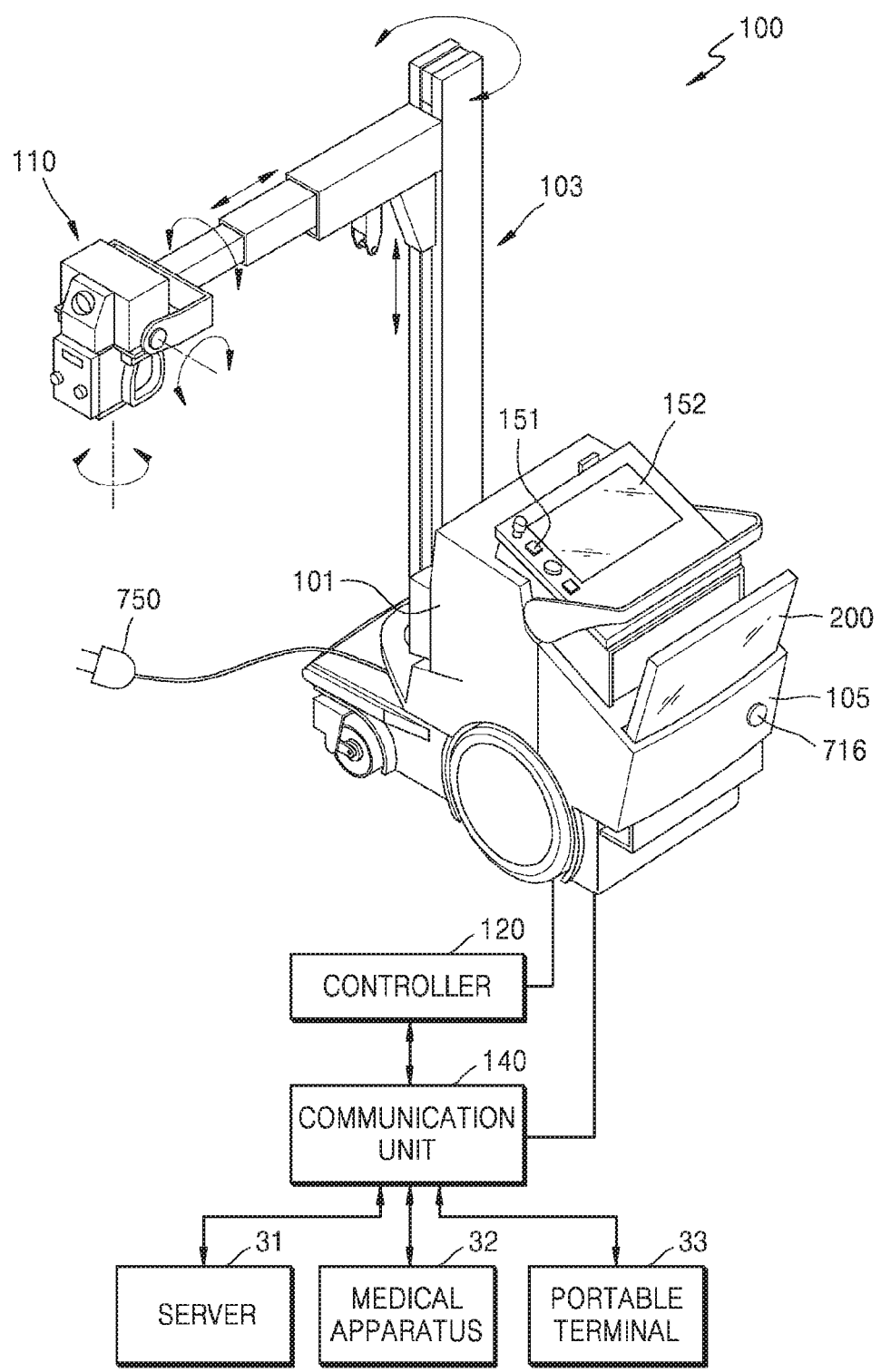
FIG. 1 illustrates an X-ray apparatus implemented as a mobile X-ray apparatus, according to an embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. As used herein, the term "and/or" includes any and all combinations of one or more of the associated listed items. Expressions such as "at least one of," when preceding a list of elements, modify the entire list of elements and do not modify the individual elements of the list. Hereinafter, the operating principles and embodiments of the present disclosure will be described in detail with reference to the accompanying drawings.

In the present specification, an image may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and include a human, an animal, or a part of a human or animal. For example, the object may include a body part (an organ, tissue, etc.) or a phantom.

FIG. 1 is an external view and block diagram of an X-ray apparatus 100 implemented as a mobile X-ray apparatus, according to an embodiment.

Referring to FIG. 1, the X-ray apparatus 100 according to the present embodiment includes an X-ray radiation device 110 for generating and emitting X-rays, an input device 151 for receiving a command from a user, a display 152 for providing information to the user, a controller 120 for controlling the X-ray apparatus 100 according to the received command, and a communication unit 140, i.e., a communication device or interface, for communicating with an external device.

The X-ray radiation device 110 may include an X-ray source for generating X-rays and a collimator for adjusting a region irradiated with the X-rays generated by the X-ray source.

When the X-ray apparatus 100 is implemented as a mobile X-ray apparatus, a main body 101 connected to the X-ray radiation device 110 is freely movable, and an arm 103 connecting the X-ray radiation device 110 and the main body 101 to each other is also rotatable and linearly movable. Thus, the X-ray radiation device 110 may be moved freely in a three-dimensional (3D) space.

The input device 151 may receive commands for controlling imaging protocols, imaging conditions, imaging timing, and locations of the X-ray radiation device 110. The input device 151 may include a keyboard, a mouse, a touch screen, a microphone, a voice recognizer, etc.

The display 152 may display a screen for guiding a user's input, an X-ray image, a screen for displaying a state of and the like.

The controller 120 may control the X-ray apparatus 100, imaging conditions and imaging timing of the X-ray radiation device 110 according to a control command input by the user and generate a medical image based on image data received from an X-ray detector 200. Furthermore, the controller 120 may control a position or orientation of the X-ray radiation device 110 according to imaging protocols and a position of an object.

The controller 120 may include a memory configured to store programs for performing the above operations of the X-ray apparatus 100 as well as operations thereof that will be described below and a processor or a microprocessor configured to execute the stored programs. The controller 120 may include a single processor or a plurality of processors or microprocessors. When the controller 120 includes the plurality of processors, the plurality of processors may be integrated onto a single chip or be physically separated from one another.

A holder 105 may be formed on the main body 101 so as to accommodate the X-ray detector 200. Furthermore, a charging terminal is disposed in the holder 105 so as to charge the X-ray detector 200. In other words, the holder 105 may be used to accommodate and also to charge the X-ray detector 200.

The input device 151, the display 152, the controller 120, and the communication unit 140 may be provided on the main body 101. Image data acquired by the X-ray detector 200 may be transmitted to the main body 101 for image processing, and then the resulting image may be displayed on the display 152 or transmitted to an external device via the communication unit 140.

Furthermore, the controller 120 and the communication unit 140 may be separate from the main body 101, or only some components of the controller 120 and the communication unit 140 may be provided on the main body 101.

The X-ray apparatus 100 may be connected to external devices such as an external server 31, a medical apparatus 32, and a portable terminal 33 (e.g., a smart phone, a tablet PC, or a wearable device) in order to transmit or receive data via the communication unit 140.

The communication unit 140 may include at least one component that enables communication with an external device. For example, the communication unit 140 may include at least one of a local area communication module, a wired communication module, and a wireless communication module Furthermore, the communication unit 140 may receive a control signal from an external device and transmit the received control signal to the controller 120 so that the controller 120 may control the X-ray apparatus 100 according to the received control signal.

Alternatively, by transmitting a control signal to an external device via the communication unit 140, the controller 120 may control the external device according to the transmitted control signal. For example, the external device may process data according to a control signal received from the controller 120 via the communication unit 140.

Furthermore, the communication unit 140 may further include an internal communication module that enables communications between components of the X-ray apparatus 100. A program for controlling the X-ray apparatus 100 may be installed on the external device and may include instructions for performing some or all of the operations of the controller 120.

The program may be preinstalled on the portable terminal 33, or a user of the portable terminal 33 may download the program from a server providing an application for installation. The server for providing an application may include a recording medium having the program recorded thereon.

In addition, the main body 101 may be equipped with an alternating current (AC) power cord 750 and/or a switch 716. The user may connect the AC power cord 750 to an outlet (not shown) when a battery management system (BMS) is shut down to wake up the BMS from shutdown. Furthermore, the user presses the switch 716 when the BMS is shut down to wake up the BMS from shutdown.

Figure 2:
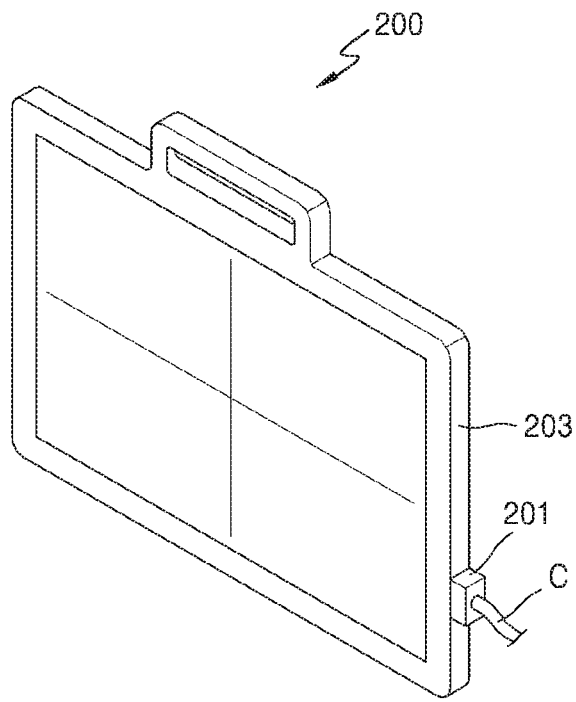
FIG. 2 illustrates an X-ray detector included in the X-ray apparatus of FIG. 1.

FIG. 2 is an external view of the X-ray detector 200.

As described above, the X-ray detector 200 used in the X-ray apparatus 100 may be implemented as a portable X-ray detector. In this case, the X-ray detector 200 may be equipped with a battery for supplying power to operate wirelessly, or as shown in FIG. 2, may operate by connecting a charge port 201 to a separate power supply via a cable C.

A case 203 maintains an external appearance of the X-ray detector 200 and has therein a plurality of detecting elements for detecting X-rays and converting the X-rays into image data, a memory for temporarily or permanently storing the image data, a communication module for receiving a control signal from the X-ray apparatus 100 or transmitting the image data to the X-ray apparatus 100, and a battery. Furthermore, image correction information and intrinsic identification (ID) information of the X-ray detector 200 may be stored in the memory, and the stored ID information may be transmitted together with the image data during communication with the X-ray apparatus 100.

Figure 3:
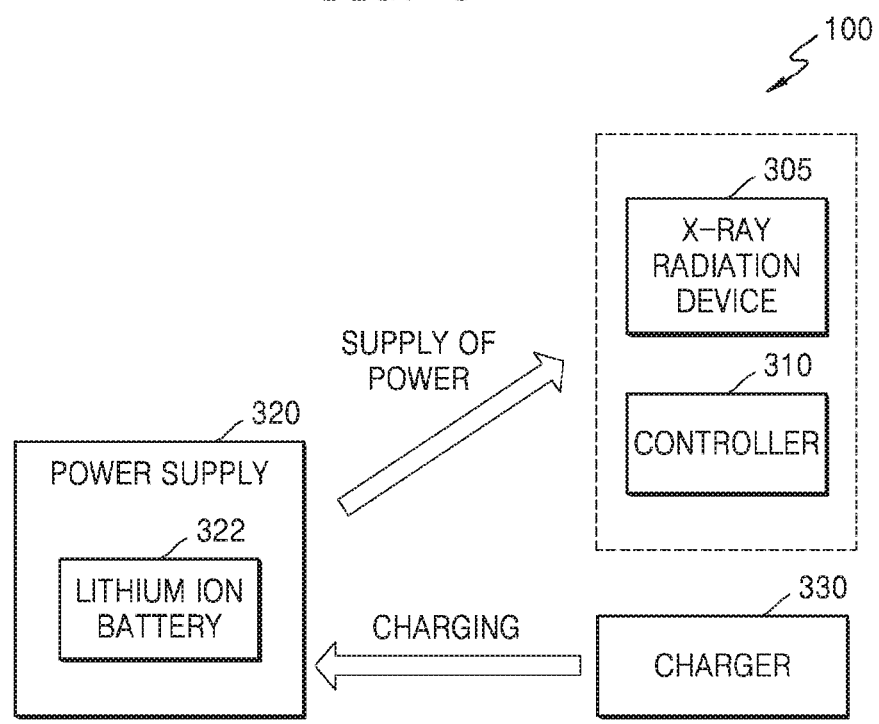
FIG. 3 is a block diagram of an X-ray apparatus according to an embodiment.

FIG. 3 is a block diagram of an X-ray apparatus 100 according to an embodiment.

Referring to FIG. 3, the X-ray apparatus 100 according to the present embodiment may include an X-ray radiation device 305, a controller 310, a power supply 320 including a lithium ion battery 322, and a charger 330. The X-ray apparatus 100 may further include a high voltage generator (not shown) provided on a main body. The X-ray apparatus 100 of FIG. 3 may be implemented as a mobile X-ray apparatus as shown in FIG. 1, and FIG. 3 illustrates only components related to the present embodiment. Thus, it will be understood by those of ordinary skill in the art that the X-ray apparatus 100 may further include common components other than those shown in FIG. 3.

The descriptions with respect to the X-ray radiation device 110 in FIG. 1 may apply to descriptions with respect to the X-ray radiation device 305, and thus, are not repeated. Furthermore, the descriptions with respect to the controller 120 in FIG. 1 may apply to descriptions with respect to the controller 310, and thus, are not repeated.

The power supply 320 may supply power to a load via the lithium ion battery 322. For example, the load may include the X-ray radiation device 305, the controller 310, and various other components of the X-ray apparatus 100, to which power is supplied. In other words, the lithium ion battery 322 may supply operating power to the X-ray radiation device 305 and the controller 310.

Furthermore, the power supply 320 may supply, via the lithium ion battery 322, operating power to components of the X-ray apparatus 100 that require the operating power. For example, the power supply 320 may supply operating power to the input device 151, the display 152, and the communication unit 140 of the X-ray apparatus 100 via the lithium ion battery 322.

The power supply 320 may control overcurrent that occurs during emission of X-rays by the X-ray radiation device 305. In other words, as the X-ray radiation device 305 emits X-rays, overcurrent that is higher than a normal operating current may flow in the power supply 320, and the power supply 320 may control the overcurrent. According to an embodiment, in order to control overcurrent, the power supply 320 may construct a circuit consisting of a discharge field effect transistor (FET) having FETs connected in parallel and a charge FET. According to another embodiment, in order to control the overcurrent, the power supply 320 may construct a circuit including current sensors having different capacities for measuring the amount of discharge current.

The charger 330 may charge the power supply 320. In detail, the charger 330 may supply a charging power to charge the lithium ion battery 322 of the power supply 320. In this case, the charging power may be a power generated by the charger 330. According to an embodiment, the charger 330 may be combined with an external power supply to receive power from the external power supply. The charger 330 may then control the received power according to a user input or arithmetic operations performed within the X-ray apparatus 100, to supply a charging power to the lithium ion battery 322.

The power supply 320, the charger 330, and the controller 310 may each include a communication interface that enables communication therebetween. For example, the power supply 320, the charger 330, and the controller 310 may communicate with one another via their communication interfaces according to a controller area network (CAN) protocol. Furthermore, according to another embodiment, communications may be performed among the power supply 320, the charger 330, and the controller 310 by using a high-speed digital interface such as low voltage differential signaling (LVDS), an asynchronous serial communication protocol such as a universal asynchronous receiver transmitter (UART), a low-latency network protocol such as an error synchronous serial communication protocol, or other various communication methods that are obvious to those of ordinary skill in the art. Furthermore, the power supply 320, the charger 330, and the controller 310 may each be constituted by a different module. Thus, since the controller 310 does not need to directly monitor a high voltage, a high voltage circuit is not needed within the controller 310. This may consequently reduce the risks associated with the high voltage circuit, thereby effectively improving stability.

In detail, in a mobile X-ray apparatus using a conventional lead-acid battery, a controller may include a circuit for monitoring a high voltage state, and may be damaged by high voltages. On the other hand, in the X-ray apparatus 100 according to the present embodiment, a BMS of the power supply 320 may monitor a high voltage state and transmit the high voltage state to the controller 310. This configuration may reduce the risk of damage to the controller 310.

Furthermore, when the power supply 320, the charger 330, and the controller 310 are each composed of a different module, they may be used for different mobile X-ray apparatuses and thus share a common platform. Furthermore, by applying a shield case to each of the power supply 320, the charger 330, and the controller 310, it is possible to suppress Electro Magnetic Interference (EMI)/Electro Magnetic Compatibility (EMC) noise that may occur therebetween.

Figure 4:
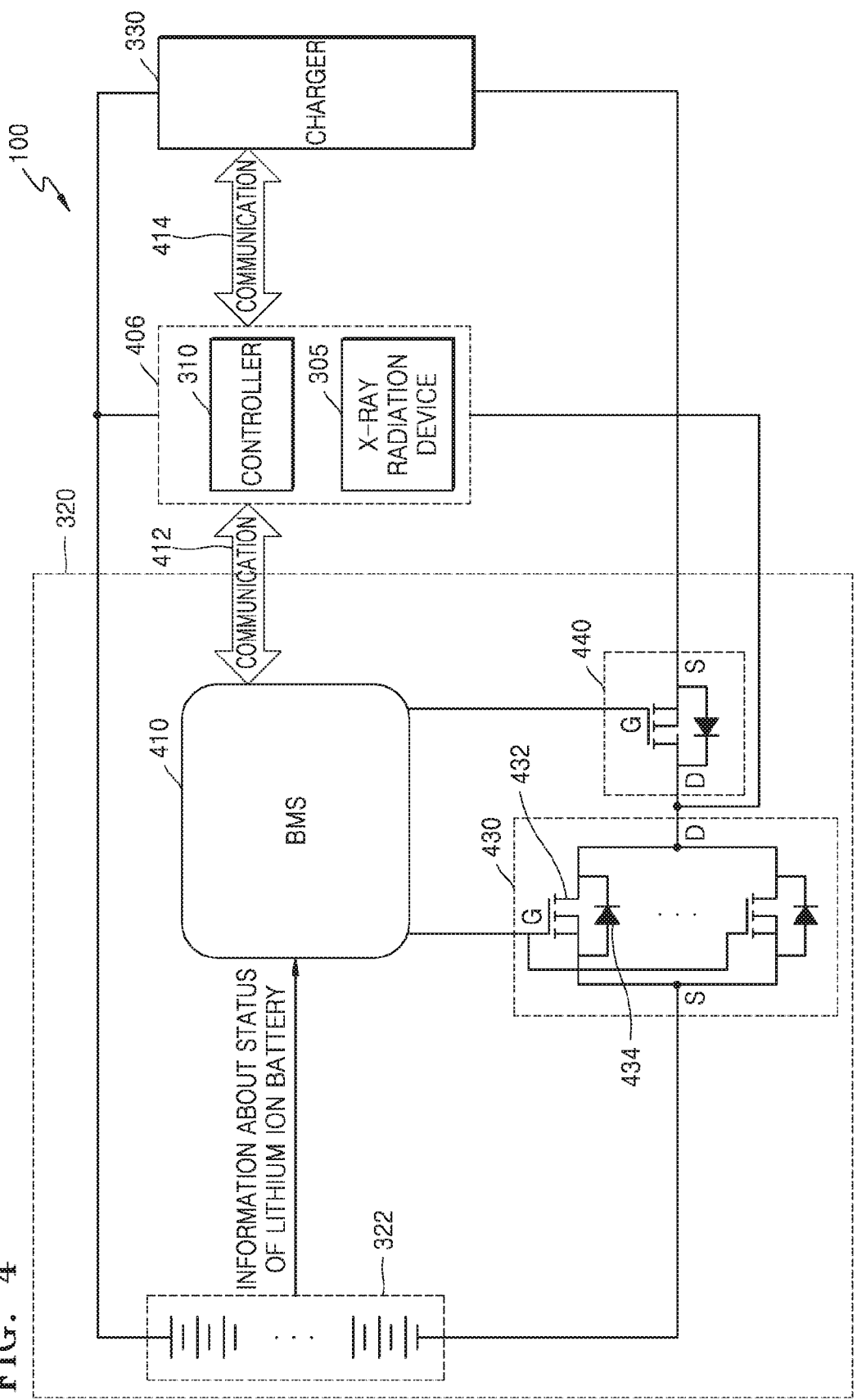
FIG. 4 illustrates components of a power supply included in a mobile X-ray apparatus, according to an embodiment.

FIG. 4 illustrates components of a power supply 320 included in a mobile X-ray apparatus 100, according to an embodiment.

Referring to FIG. 4, the power supply 320 may include a lithium ion battery 322, a BMS 410, a discharge FET 430, and a charge FET 440. The power supply 320 shown in FIG. 4 includes only components related to the present embodiment. Furthermore, the power supply 320 may include a voltage sensor (not shown) for detecting a voltage and a temperature sensor (not shown) for detecting a temperature. Thus, one of ordinary skill in the art will understand that the power supply 320 may further include common components other than those shown in FIG. 4.

The lithium ion battery 322 is a type of secondary battery and consists of three components: an anode, a cathode, and an electrolyte. For example, lithium cobalt oxide ($LiCoO_2$) or lithium iron phosphate ($LiFePO_4$) may be used for the anode, and graphite may be used for the cathode. The lithium ion battery 322 may include a combination of a plurality of battery cells connected to each other. For example, the lithium ion battery 322 may include a total of 352 cells, e.g., a serial connection of 88 cells which are connected in parallel as 4 strings, e.g., 4 parallel cell groups each including 88 serially connected cells.

Furthermore, the lithium ion battery 322 may be suitable for use in a mobile X-ray apparatus due to its smaller size and lighter weight than conventional lead-acid batteries. For example, since a total weight of the power supply 330 including the lithium ion battery 322 and a peripheral circuit may be 33.2 kg, the total weight may be less than 35 kg, which is the maximum allowable gross weight for carrying on an aircraft. Thus, the power supply 320 may be transported by air as a single component.

The mobile X-ray apparatus 100 may supply power to an X-ray radiation device 305 through a battery, and may include the BMS 410 configured to operate a protection circuit by checking a voltage and a temperature of the battery.

The BMS 410 may detect a state of the lithium ion battery 322, such as a voltage and a temperature thereof. According to an embodiment, the BMS 410 may include a battery stack monitor circuit designed to monitor a voltage of the lithium ion battery 322 and a temperature of a battery cell. The BMS 410 may control and manage the power supply 320 based on the state of the lithium ion battery 322. Furthermore, the BMS 410 may control on/off states of the charge FET 440 and the discharge FET 430 to manage a charge path and a discharge path, respectively.

Furthermore, the BMS 410 may operate a protection circuit based on the state of the lithium ion battery 322. In other words, the BMS 410 may operate, based on the state of the lithium ion battery 322, the protection circuit to protect the lithium ion battery 322 from dangerous conditions. In detail, based on the state of the lithium ion battery 322, the BMS 410 may operate the protection circuit to protect the lithium ion battery 322 against at least one of over-discharge, overcurrent, overheating, and unbalancing between battery cells.

The BMS 410 may operate, based on the state of the lithium ion battery 322, the protection circuit by checking states of over-discharge, overcurrent, overheating, and unbalancing between battery cells, and may accordingly be shut down.

The BMS 410 may operate the protection circuit when the lithium ion battery 322 is in an over-discharged state where a voltage of the lithium ion battery 322 is lower than a reference voltage. For example, if a voltage of the lithium ion battery 322 drops to less than or equal to 275 V, the BMS 410 may operate a shutdown circuit to turn itself off. Furthermore, the BMS 410 may operate the protection circuit when the lithium ion battery 322 is in an overcurrent state where a current of the lithium ion battery 322 is higher than a reference value. For example, if the current of the lithium ion battery 322 is greater than or equal to 40 A, the BMS 410 may operate a shutdown circuit to reset itself. The BMS 410 may also operate the protection circuit when the lithium ion battery 322 is in an overheated state where a temperature of the lithium ion battery 322 is higher than a reference value. For example, if the temperature of the lithium ion battery 322 is greater than or equal to 70° C., the BMS 410 may operate the protection circuit to shut off a charge path and a discharge path. Furthermore, when the lithium ion battery 322 is unbalanced between cells, the BMS 410 may operate the protection circuit. For example, if a voltage difference between cells in the lithium ion battery 322 remains greater than or equal to 0.5 V for ten (10) seconds or more, the BMS 410 may operate a shutdown circuit to turn itself off.

The BMS 410 may communicate with a controller 310 via a communication interface 412, e.g., according to a CAN protocol. Further, the charger 330 may communicate with the controller 310 via a communication interface 414, e.g., according to the CAN protocol.

A load 406 may receive power via a charge path and/or a discharge path.

The discharge FET 430 may include a plurality of FETs 432 connected in parallel. Since overcurrent may flow in the power supply 320 during X-ray emission by the X-ray radiation device 305, the FETs having a specific capacity in the discharge FET 430 may be connected in parallel. In other words, by connecting the FETs having the specific capacity in parallel, a maximum allowable current capacity of the discharge FET 430 may be increased. For example, if overcurrent greater than or equal to 300 A flows within the power supply 320 during X-ray emission by the X-ray radiation device 305, the discharge FET 430 may include 4 FETs which are connected in parallel and have a capacity of 100 A each for the protection against the overcurrent.

According to an embodiment, the discharge FET 430 and the charge FET 440 may each be constituted by an N-channel FET.

The discharge FET 430 and the charge FET 440 may control a path of discharge or charge current when the lithium ion battery 322 is discharged or charged. According to an embodiment, when the lithium ion battery 322 is discharged, the charge FET 440 may be turned off, and a discharge current loop may be formed by the discharge FET 430. According to another embodiment, when the lithium ion battery 322 is charged, the discharge FET 430 may be turned off, and a charge current loop may be formed by a diode or diodes 434 included in the discharge FET 430 and the charge FET 440. Furthermore, the lithium ion battery 322 may be discharged and charged at the same time via the discharge FET 430 and the charge FET 440.

Furthermore, while FIG. 4 shows that a load 406 for receiving a power from the lithium ion battery 322 includes the controller 310 and the X-ray radiation device 305, the load 406 may further include other components of the X-ray apparatus 100 that require power.

Figure 5:
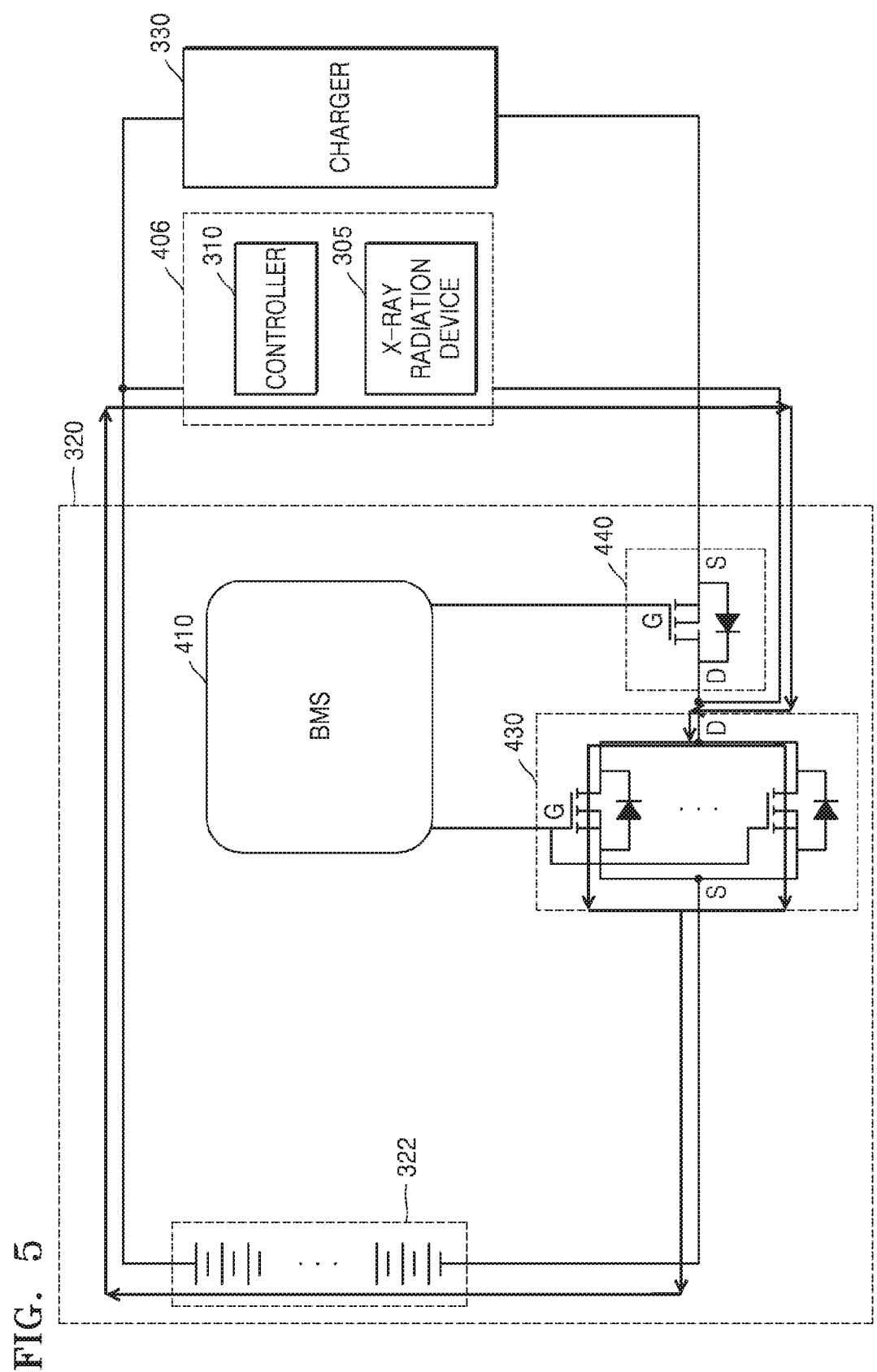
FIG. 5 is a schematic diagram illustrating discharging of a lithium ion battery according to an embodiment.

FIG. 5 is a schematic diagram illustrating discharging of a lithium ion battery 322 according to an embodiment.

An on/off state of a discharge FET 430 may be controlled based on a signal output from a BMS 410. In detail, the discharge FET 430 may be turned on when the lithium ion battery 322 is discharged and be turned off when the lithium ion battery 322 is charged. The signal may be coupled to a gate terminal of the discharge FET 430. When the discharge FET 430 is turned off, a current path is formed from a minus terminal of the lithium ion battery 322 to a charger 330 via a body diode.

In detail, when the lithium ion battery 322 is discharged, a charge FET 440 may be turned off since a source (S) voltage of the charge FET 440 is higher than a drain (D) voltage thereof. Furthermore, when the lithium ion battery 322 is discharged, a discharge FET 430 may be turned on since a drain (D) voltage of the discharge FET 430 is higher than a source (S) voltage thereof.

Thus, as shown in FIG. 5, a discharge current loop may be formed in a clockwise direction in which a discharge current flows through a load 406, the discharge FET 430, and the lithium ion battery 322. Furthermore, even when the charge FET 440 is turned off, discharging of the lithium ion battery 322 may be performed normally.

Figure 6:
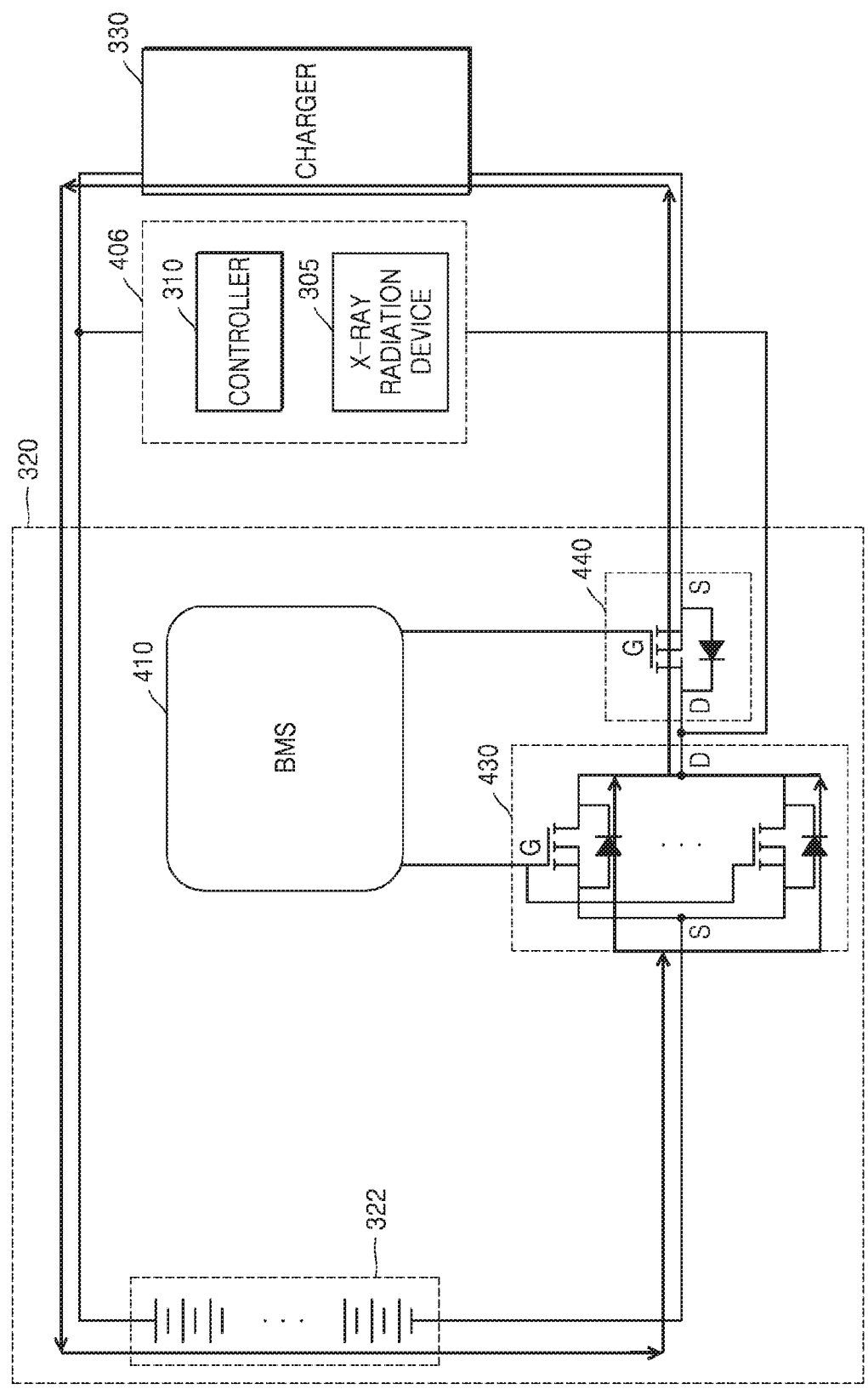
FIG. 6 is a schematic diagram illustrating charging of a lithium ion battery according to an embodiment.

FIG. 6 is a schematic diagram illustrating charging of a lithium ion battery 322 according to an embodiment.

An on/off state of a charge FET 440 may be controlled based on a signal output from a BMS 410. In detail, the charge FET 440 may be turned on when the lithium ion battery 322 is charged and be turned off when the lithium ion battery 322 is discharged. When the charge FET 440 is turned off, a current path from the load 406 to a minus terminal of the lithium ion battery 322 may be formed.

In detail, when the lithium ion battery 322 is charged, a discharge FET 430 may be turned off since a source (S) voltage of the discharge FET 430 is higher than a drain (D) voltage thereof. When the discharge FET 430 is turned off, a charge current may flow through a body diode of the discharge FET 430. Furthermore, when the lithium ion battery 322 is charged, the charge FET 440 may be turned on since a drain (D) voltage of the charge FET 440 is higher than a source (S) voltage thereof.

Thus, as shown in FIG. 6, a charge current loop may be formed in a counter-clockwise direction in which a charge current flows through a charger 330, the lithium ion battery 322, a diode 434 of the discharge FET 430, and the charge FET 440. Furthermore, even when the discharge FET 430 is turned off, charging of the lithium ion battery 322 may be performed normally.

Figure 7:
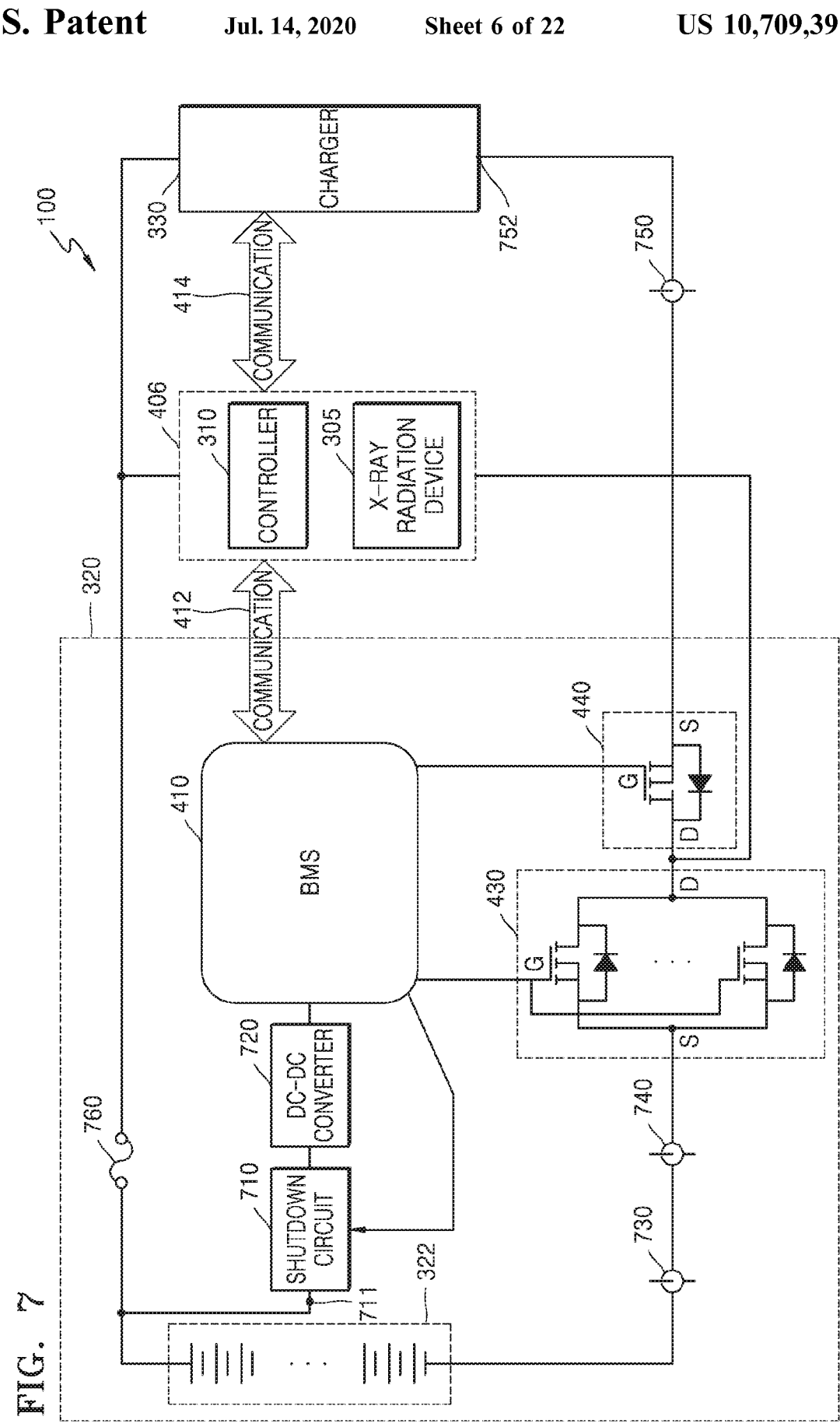
FIG. 7 is a detailed block diagram of a mobile X-ray apparatus according to an embodiment.

FIG. 7 is a detailed block diagram of a mobile X-ray apparatus 100 according to an embodiment.

Referring to FIG. 7, a power supply 320 may include a lithium ion battery 322, a BMS 410, a discharge FET 430, a charge FET 440, a shutdown circuit 710, a first current sensor 730, a second current sensor 740, a DC-to-DC (DC-DC) converter 720, and a fuse 760. Furthermore, the X-ray apparatus 100 may include a third current sensor 751. Since the lithium ion battery 322, the BMS 410, the discharge FET 430, and the charge FET 440 respectively correspond to the lithium ion battery 322, the BMS 410, the discharge FET 430, and the charge FET 440 described with reference to FIG. 4, detailed descriptions thereof will be omitted below. The first and second current sensors 730 and 740 may include a Hall sensor, and the shutdown circuit 710 that is a protection circuit may include a switching circuit such as a FET.

The BMS 410 may detect current of the lithium ion battery 322 by using different current sensors, i.e., the first and second current sensors 730 and 740. In detail, the BMS 410 may detect current flowing in the lithium ion battery 322 by using the first current sensor 730. The first current sensor 730 may be a small-capacity sensor for detecting a current having a relatively low intensity. In other words, the first current sensor 730 may be a sensor for detecting a current having an intensity less than or equal to a reference level. For example, the first current sensor 730 may detect a current that is less than or equal to 50 A. Furthermore, when overcurrent flows in the lithium ion battery 322, the BMS 410 may detect overcurrent flowing in the lithium ion battery 322 by using the second current sensor 740. The second current sensor 740 may be a large-capacity sensor for detecting a current having a relatively high intensity. In other words, the second current sensor 740 may be a sensor for detecting a current having an intensity greater than or equal to a reference level. For example, the second current sensor 740 may detect a current that is greater than or equal to 300 A.

According to an embodiment, the BMS 410 may detect, via the first current sensor 730, current flowing in the lithium ion battery 322 by activating the first current sensor 730 while deactivating the second current sensor 740. Then, when an X-ray radiation device 305 emits X-rays, the BMS 410 may detect overcurrent that occurs during the X-ray emission via the second current sensor 740 by activating the second current sensor 740 while deactivating the first current sensor 730. Subsequently, when the X-ray emission is completed, the BMS 410 may detect, via the first current sensor 730, current flowing in the lithium ion battery 322 by activating the first current sensor 730 while deactivating the second current sensor 740. According to an embodiment, the BMS 410 may receive an X-ray emission preparation signal from a controller 310 and activate the second current sensor 740 to detect overcurrent occurring during X-ray emission via the second current sensor 740.

The BMS 410 may check the residual amount of the lithium ion battery 322 based on the amount of current detected using the first and second current sensors 730 and 740. In detail, the BMS 410 may use Coulomb Counting Based Gauging to check the residual amount of the lithium ion battery 322 based on the detected amount of current.

Furthermore, the mobile X-ray apparatus 100 may further include the third current sensor 751 for measuring a charge current. In other words, the mobile X-ray apparatus 100 may further include the third current sensor 751 at an output terminal 752 of the charger 330. When the lithium ion battery 322 is charged and discharged at the same time, current measured by the first or second current sensor 730 or 740 may be a sum of a discharge current and a charge current. Thus, in order to accurately measure a discharge current and a charge current, the mobile X-ray apparatus 100 may measure the charge current by using the third current sensor 751.

The BMS 410 may receive signals indicating that the X-ray radiation device 305 starts emission of X-rays and that the X-ray radiation device 305 completes the emission of X-rays from the controller 310 via a communication interface 412.

The BMS 410 may output a first signal based on a state of the lithium ion battery 322. The first signal may be a shutdown signal that is applied to the shutdown circuit 710. The BMS 410 may turn itself off by using the shutdown circuit 710. When the BMS 410 checks a state of the lithium ion battery 322 to detect hazardous conditions such as over-discharge and overcharge, the BMS 410 may turn itself off by using the shutdown circuit 710 that serves as a protection circuit. When the BMS 410 turns itself off, power being supplied to the controller 310 is also cut off, so that the controller 310 may also turn off.

The fuse 760 is designed to stop continuous flowing of excessive current that is greater than a nominal value in the power supply 320 and may protect a battery cell when the lithium ion battery 322 is subjected to an external short circuit.

The DC-DC converter 720 may convert power supplied by the lithium ion battery 322 into a DC power for driving the BMS 410.

Figure 8:
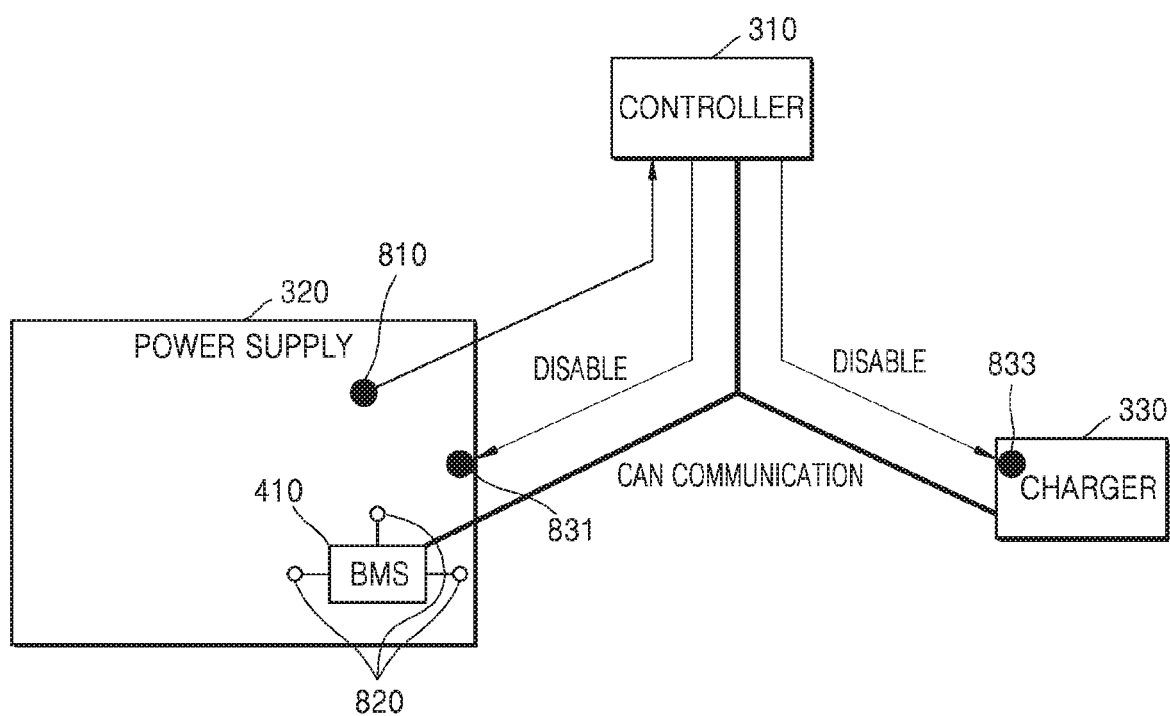
FIG. 8 illustrates a shutdown process performed by a mobile X-ray apparatus according to an embodiment.

FIG. 8 illustrates a shutdown process performed by the mobile X-ray apparatus 100 according to an embodiment. The shutdown process will now be described with reference to FIGS. 7 and 8.

Referring to FIGS. 7 and 8, the power supply 320, the controller 310, and the charger 330 may each include a communication interface and communicate with one another via their communication interfaces. For example, the power supply 320, the controller 310, and the charger 330 may communicate with one another according to a CAN protocol.

The power supply 320 may include a first temperature sensor 820. According to an embodiment, the power supply 320 may include the first temperature sensor 820 that is dedicated for use with the BMS 410 and may be directly monitored by the BMS 410. The BMS 410 may use the first temperature sensor 820 to monitor a temperature of the power supply 320 and determine whether the power supply 320 is overheated. For example, if the power supply 320 is overheated to a temperature higher than a specific threshold value, the BMS 410 may control the charge FET 440 that is a charge controller and the discharge FET 430 that is a discharge controller to cut off a charge path and a discharge path and control a protection circuit to turn off the BMS 410 itself.

Furthermore, the power supply 320 may further include a second temperature sensor 810. According to an embodiment, the power supply 320 may include the second temperature sensor 810 that is dedicated for use with the controller 310 and may be directly monitored by the controller 310. The second temperature sensor 810 may be provided on outside of the BMS 410. If a communication error occurs between the controller 310 and the BMS 410, the controller 310 may not be able to receive temperature information of the power supply 320 from the BMS 410. In this case, the controller 310 may monitor the temperature of the power supply 320 via the second temperature sensor 810. Thus, when a communication error occurs, the controller 310 may determine whether to turn off the power supply 320 by using the second temperature sensor 810 regardless of the state of the BMS 410.

The power supply 320 and the charger 330 may respectively include interrupt pins 831 and 833 that can be directly controlled by the controller 310. In other words, the controller 310 may respectively transmit disable signals to the power supply 320 and the charger 330 via the interrupt pins 831 and 833, and accordingly turn off the power supply 320 and the charger 330. Thus, when it is determined that a temperature of the power supply 320 is equal to or higher than a specific threshold value via the second temperature sensor 810, the controller 310 may forcibly turn off the power supply 320 and the charger 330 via the interrupt pins 831 and 833, respectively.

Furthermore, when the BMS 410 operates a shutdown circuit that is a protection circuit to turn itself off, a shutdown signal from the BMS 410 may be transmitted to the controller 310. After receiving the shutdown signal, the controller 310 may monitor whether the BMS 410 is shut down for a specific amount of time. If the BMS 410 is not shut down for the specific amount of time as a result of monitoring, the controller 310 may forcibly turn off the BMS 410 via the interrupt pin 831. For example, after the BMS 410 activates a shutdown bit, the controller 310 may monitor whether the BMS 410 is shut down for ten (10) seconds. If the BMS 410 is not shut down for 10 seconds, the controller 310 may forcibly turn off the BMS 410 via the interrupt pin 831.

Figure 9:
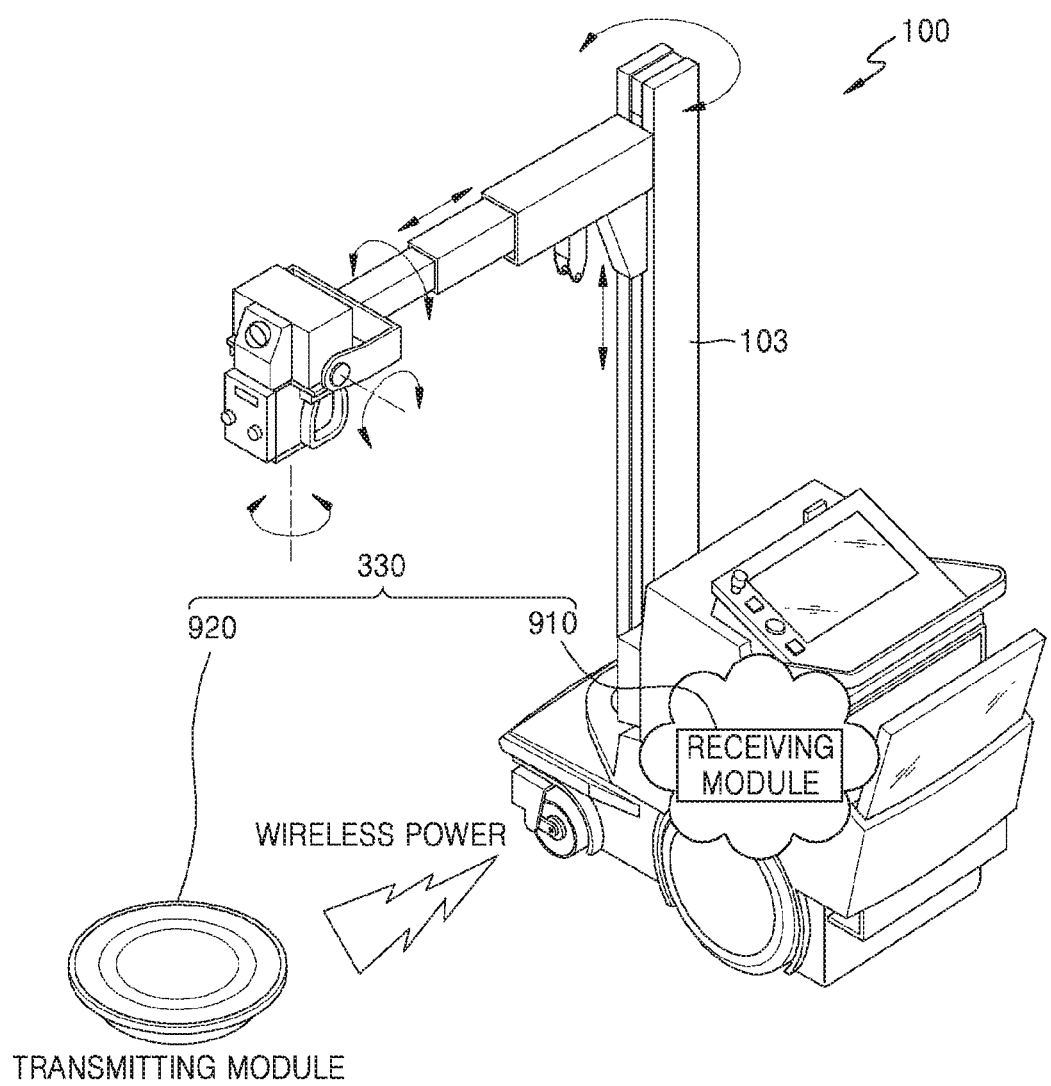
FIG. 9 illustrates a charger according to an exemplary embodiment.

FIG. 9 illustrates an X-ray apparatus according to an exemplary embodiment.

According to an exemplary embodiment, the charger 330 may include a wireless charging system including a transmitting module 920, e.g., a transmitter, and a receiving module 910, e.g., a receiver. For example, the charger 330 may be a self-inductive wireless charging system. In the charger 330, the transmitting module 920 may convert an AC power from an external power supply into a DC power, amplify the DC power, and transmit the amplified DC power wirelessly to the receiving module 910 via a transmitting coil. The receiving module 910 may rectify the received power to charge the lithium ion battery 322.

As another example, the receiving module 910 of the charger 330 may receive a power transmitted wirelessly by the transmitting module 920 installed externally to the receiving module 910 and may rectify the received power to charge the lithium ion battery 322. Thus, an X-ray apparatus 100 including the charger 330 may be located near the transmitting module 920 and may charge the lithium ion battery 322 by using the power transmitted wirelessly by the transmitting module 920.

Figure 10:
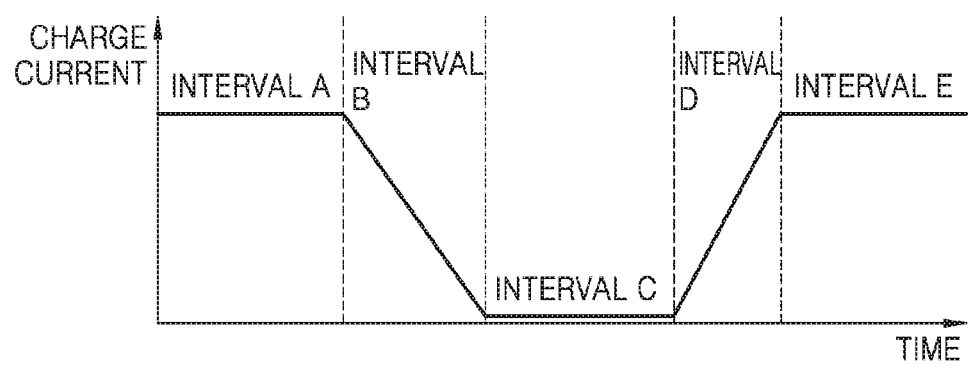
FIG. 10 is a timing diagram of an operation of charging a lithium ion battery according to an exemplary embodiment.

FIG. 10 is a timing diagram of an operation of charging a lithium ion battery 322 according to an exemplary embodiment.

First, during interval A, as the charger 330 performs a charging operation, a charge voltage may increase while a charge current remains constant.

Thereafter, during interval B, as the lithium ion battery 322 relaxes, the charge current may decrease.

An interval C indicates a low current state in which a charge current less than a specific threshold value remains for a specific amount of time. The charger 330 may detect the low current state, as will be described in detail below with reference to FIG. 11. If the low current state is detected for a specific amount of time or a specific number of times, the charger 330 may stop a charging operation. For example, if the charger 330 detects a low current state, in which the charge current is less than or equal to 0.5 A, 10 times, the charger 330 may stop a charging operation. Thus, if the lithium ion battery 322 relaxes, the charger 330 may stop the charging operation, thereby preventing unnecessary power consumption.

Subsequently, during interval D, when a voltage of the lithium ion battery 322 drops to a preset value, the charger 330 may restart the charging operation, and the charge current may also increase.

Thereafter, during interval E, which corresponds to the interval A, as the charger 330 performs the charging operation, the charge voltage may increase while the charge current remains constant.

Figure 11:
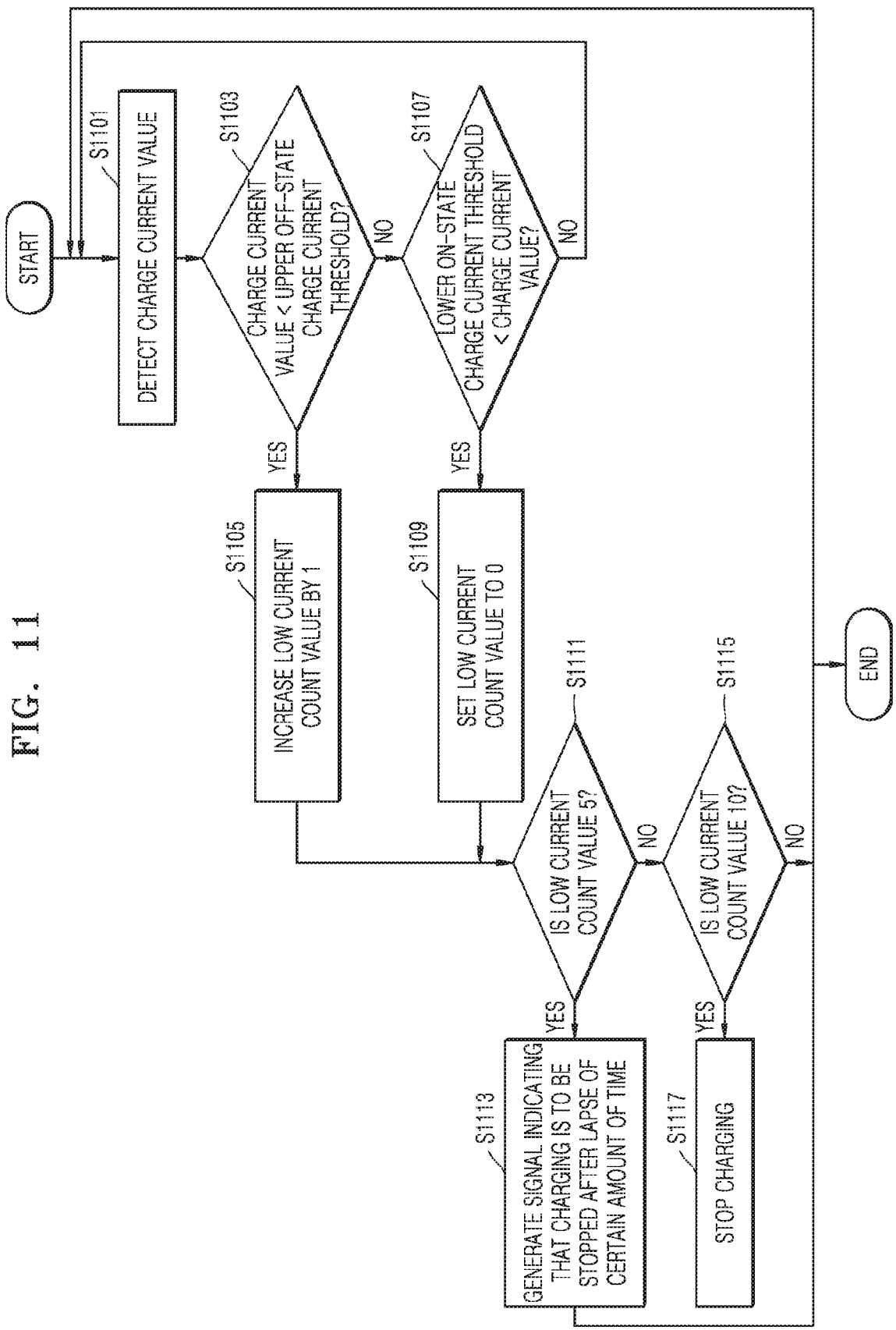
FIG. 11 is a flowchart of a method of sensing of a low current state by a charger, according to an exemplary embodiment.

FIG. 11 is a flowchart of a method of sensing of a low current state by the charger 330, according to an exemplary embodiment.

The charger 330 may detect a charge current value (operation S1101).

The charger 330 may determine whether the detected charge current value is less than an upper off-state charge current threshold (operation S1103). For example, the upper off-state charge current may be 0.5 A.

If the detected charge current value is less than the upper off-state charge current threshold in operation S1103, the charger 330 may increase a low current count value by 1 (operation S1105). In other words, if the low current count value is increased by 1 each cycle to reach a certain count value, e.g., 10, the charger 330 may determine that the current has remained low for a certain amount of time.

Otherwise, if the detected charge current value is not less than the upper off-state charge current threshold in operation S1103, the charger 330 may determine whether the detected charge current value is greater than a lower on-state charge current threshold (operation S1107). For example, the lower on-state charge current threshold may be 0.8 A.

If the detected charge current value is greater than the lower on-state charge current threshold in operation S1107, the charger 330 may set the low current count value to 0 (operation S1109).

Otherwise, if the detected charge current value is not greater than the lower on-state charge current threshold in operation S1107, the charger 330 may detect a charge current value (operation S1101).

The charger 330 may determine whether the low current count value is five 5 (operation S1111).

If the low current count value is 5 in operation S1111, the charger 330 may generate a signal indicating that a charging operation is to be stopped after a lapse of a certain amount of time (operation S1113).

Otherwise, if the low current count value is not 5 in operation S1111, the charger 330 may determine whether the low current count value is 10 (operation S1115).

If the low current count value is 10 in operation S1115, the charger 330 may stop the charging operation (operation S1117). In other words, if the low current count value is 10, the charger 330 may determine that the low current state has remained for the certain amount of time and then stop the charging operation.

Otherwise, if the low current count value is not 10 in operation S1115, the charger 330 may detect a charge current value (operation S1101).

Figure 12:
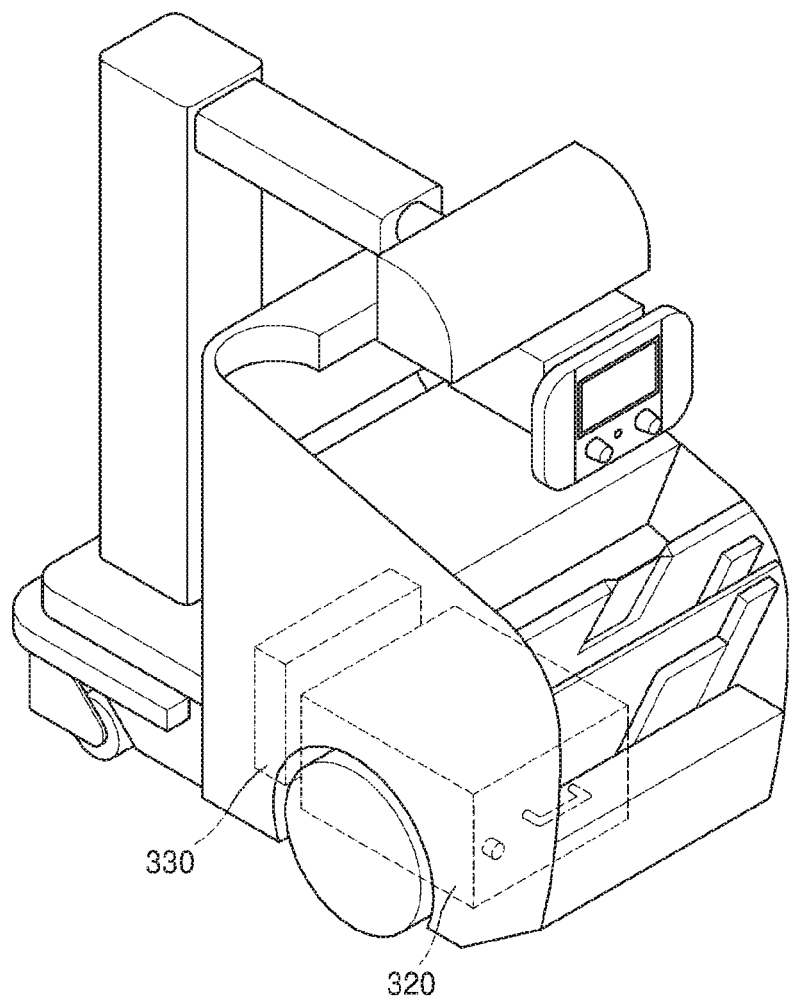
FIG. 12 illustrates an X-ray apparatus according to an embodiment.

FIG. 12 is an external/internal perspective view of an X-ray apparatus 100 according to an embodiment.

Referring to FIG. 12, a power supply 320 and a charger 330 are arranged inside the X-ray apparatus 100.

The power supply 320 weighs approximately 33.2 kg and may be arranged in a lower part of the X-ray apparatus 100. Thus, since a center of gravity of the X-ray apparatus 100 may be located at the bottom thereof, the X-ray apparatus 100 may be moved stably.

The power supply 320 may be encased in a metal case and be provided as a module that is physically separated from other components.

An internal structure of the power supply 320 will be described in detail below with reference to FIGS. 20 through 25.

The charger 330 receives an AC power to charge a lithium ion battery within the power supply 320. The charger 330 may be shielded by a shield case and provided as a separate module. The charger 330 may be positioned at a front surface of the power supply 320.

Figure 13:
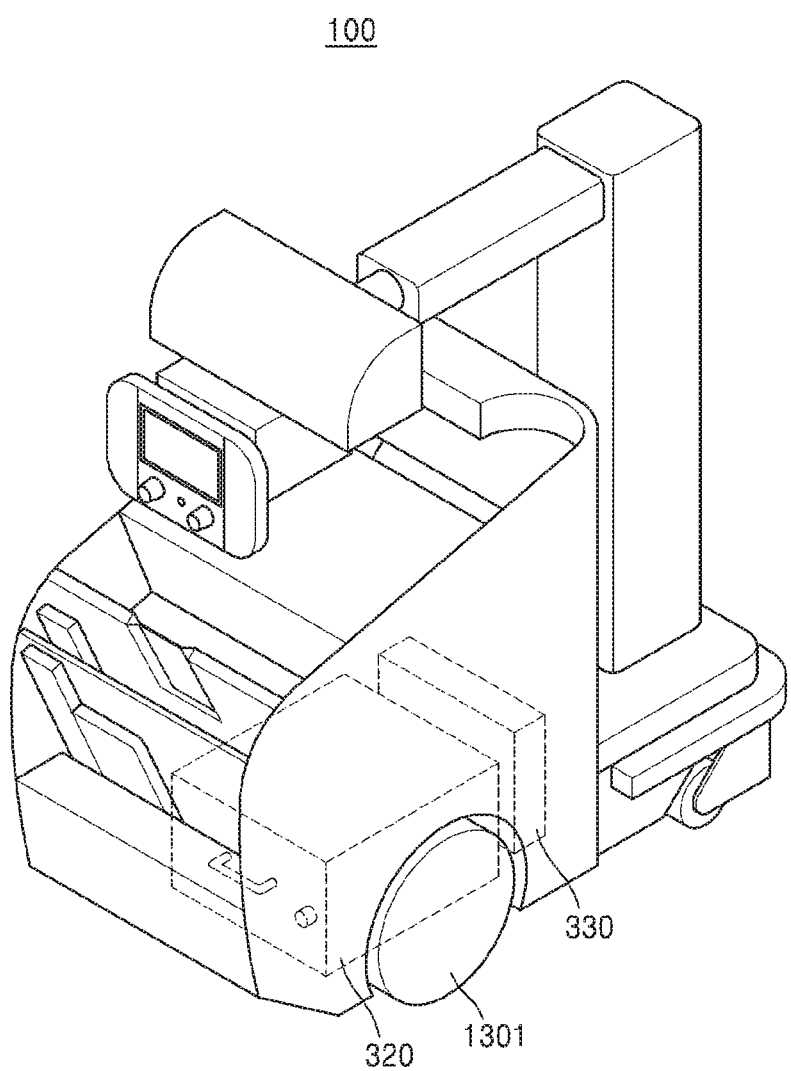
FIG. 13 illustrates an X-ray apparatus, according to an embodiment.

FIG. 13 is an external/internal perspective view of an X-ray apparatus 100 taken from a different angle, according to an embodiment.

Referring to FIG. 13, a power supply 320 and a charger 330 are arranged inside the X-ray apparatus 100.

Since the power supply 320 and the charger 330 are arranged in the same manner as described with reference to FIG. 12, a detailed description thereof will be omitted below.

Figure 14:
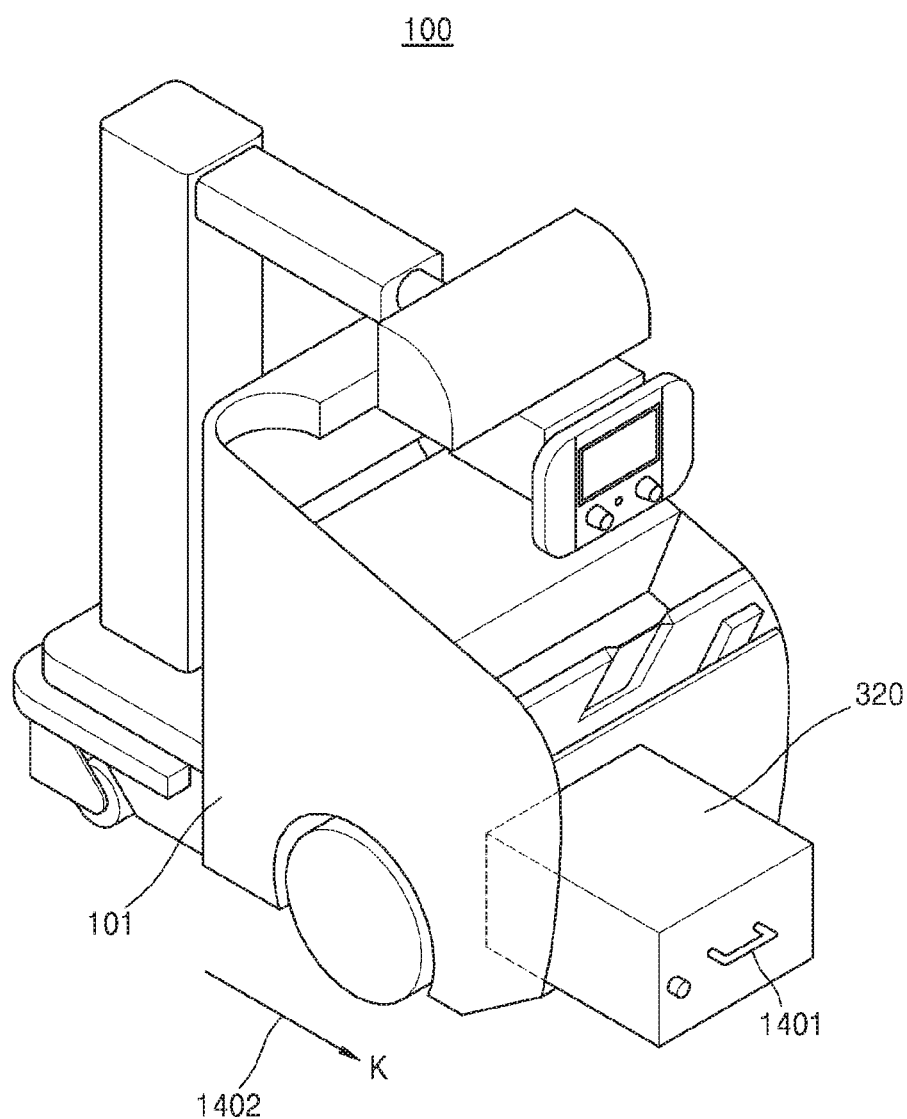
FIG. 14 illustrates a state in which a power supply is detached from an X-ray apparatus, according to an embodiment.

FIG. 14 illustrates a state in which a power supply 320 is detached from an X-ray apparatus 100, according to an embodiment.

The power supply 320 may include a handle 1401 and may be detached from a main body 101 of the X-ray apparatus 100. A user may use the handle 1401 to separate the power supply 320 from or mount it into the main body 101 of the X-ray apparatus 100. The power supply 320 may include two handles 1401 that allow the user to separate the power supply 320 from the main body 101 or lift and move the power supply 320.

For example, the user may pull the power supply 320 along a K direction 1402 and separate it from the main body 101.

Figure 15:
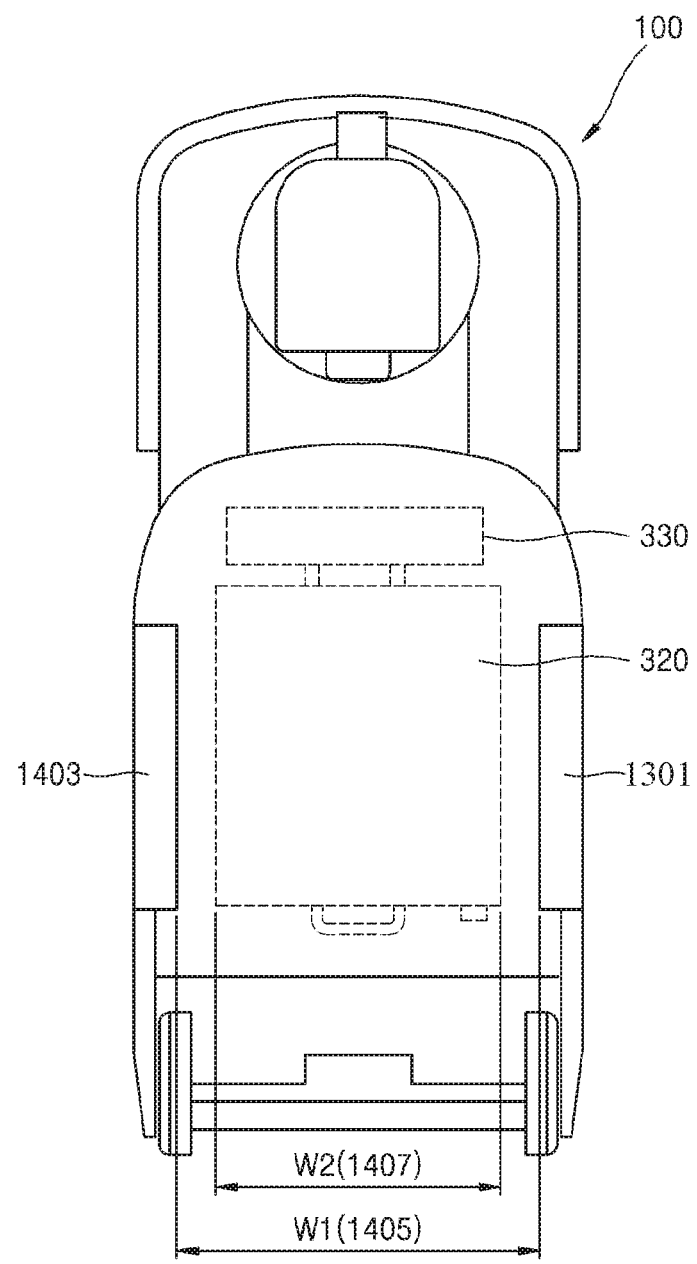
FIG. 15 illustrates an X-ray apparatus according to an embodiment.

FIG. 15 is an external/internal plan view of an X-ray apparatus 100 according to an embodiment.

Referring to FIG. 15, the X-ray apparatus 100 includes wheels 1301 and 1403, a power supply 320, and a charger 330.

The power supply 320 may be provided between the wheels 1301 and 1403, so that a width W1 1405 of the X-ray apparatus 100 may be decreased. Furthermore, a width W2 1407 of the power supply 320 may be less than the width W1 1405.

Figure 16:
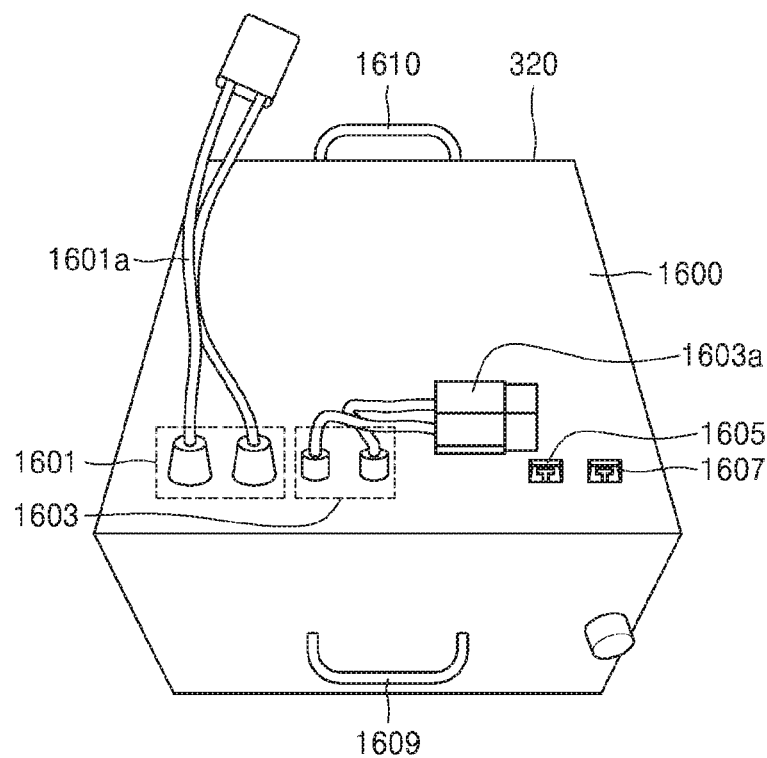
FIG. 16 illustrates a power supply according to an embodiment.

FIG. 16 is an external view of a power supply 320 according to an embodiment.

Referring to FIG. 16, the power supply 320 may include an external case 1600, a discharging terminal 1601, a charging terminal 1603, a first communication connector 1605, a second communication connector 1607, and handles 1609 and 1610.

The external case 1600 may be made of metal, and protect the power supply 320 against external shocks and function as a shield case that blocks electromagnetic waves from entering or exiting the power supply 320.

The discharging terminal 1601 is connected to a cable 1601a to supply power output from a battery cell in the power supply 320 to an X-ray radiation device.

The charging terminal 1603 is connected to a charging power supply terminal (1801 of FIG. 18) of a charger (330 of FIG. 18) and a cable 1603a to receive power necessary for charging a battery.

The second communication connector 1607 is connected to a charger and a controller via a cable (not shown) so that the power supply 320 may perform communications with the charger and the controller. For example, the power supply 320 may communicate with the charger and the controller according to a CAN protocol via the cable connected to the second communication connector 1607.

Furthermore, the user may use the second communication connector 1607 and the cable to update firmware for the power supply 320 without separating the power supply 320 from an X-ray apparatus. For example, when the power supply 320 is mounted into the X-ray apparatus, the user may transmit data necessary to update the firmware for the power supply 320 via the controller of the X-ray apparatus.

The power supply 320 may include the first communication connector 1605 that is, for example, a RS232C port. When the power supply 320 is separated from the X-ray apparatus, the firmware for the power supply 320 may be updated via the first communication connector 1605.

Handles 1609 and 1610 may be folding handles, but are not limited thereto. Various types of handles may be used as the handles 1609 and 1610. Examples of the handles 1609 and 1610 may include permanent magnetic handles, removable handles, handles using concave portions formed in the external case 1600, outward-protruding handles, etc. Furthermore, while FIG. 16 shows that the power supply 320 is equipped with the two handles 1609 and 1610, the number of handles may vary according to embodiments.

Figure 17:
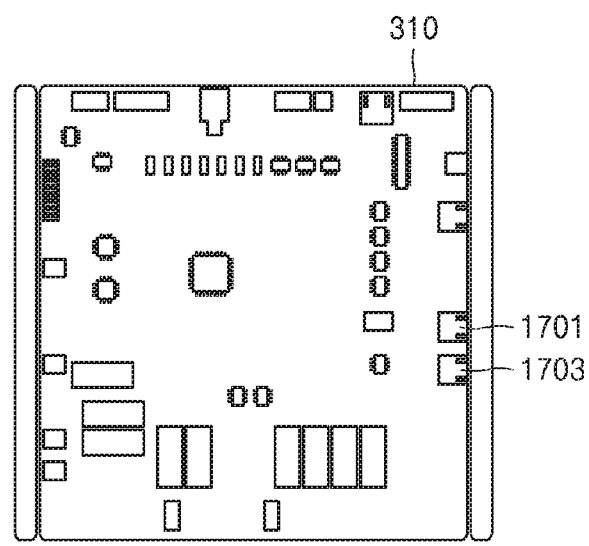
FIG. 17 is an example of a controller according to an embodiment.

FIG. 17 is an example of a controller 310 according to an embodiment.

The controller 310 may be composed of a plurality of printed circuit boards (PCBs).

The controller 310 may include various blocks for operating an X-ray apparatus.

Figure 18:
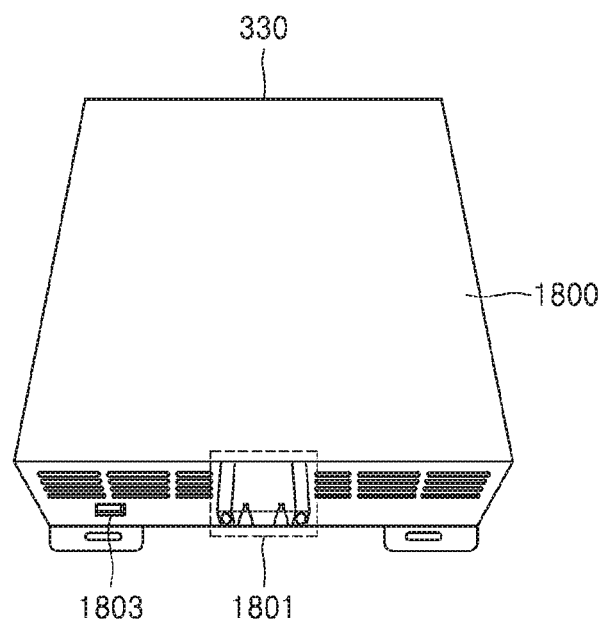
FIG. 18 illustrates a charger according to an embodiment.

In particular, the controller 310 may include a third communication connector 1701 and a fourth communication connector 1703 for respectively performing communications with the power supply (320 of FIG. 16) and the charger (330 of FIG. 18).

The third communication connector 1701 is connected to the second communication connector (1607 of FIG. 16) of the power supply 320 so that the controller 310 may communicate with the power supply 320 according to a CAN protocol.

The fourth communication connector 1703 is connected to a fifth communication connector (1803 of FIG. 18) of the charger 330 so that the controller 310 may communicate with the charger 330 according to the CAN protocol.

FIG. 18 is an external view of the charger 330 according to an embodiment.

Referring to FIG. 18, the charger 330 may include an external case 1800, the fifth communication connector 1803, and the charging power supply terminal 1801.

The external case 1800 may be made of metal, and protect the charger 330 against external shocks and serve as a shield case that blocks electromagnetic waves from entering or exiting the charger 330. The fifth communication connector 1803 is connected to the fourth communication connector (1703 of FIG. 17) of the controller (310 of FIG. 17) so that the charger 330 may communicate with the controller 310 according to a CAN protocol. Furthermore, the charger 330 may update its firmware via the fifth communication connector 1803.

The charging power supply terminal 1801 may supply power to the charging terminal (1603 of FIG. 16) of the power supply 320.

Figure 19:
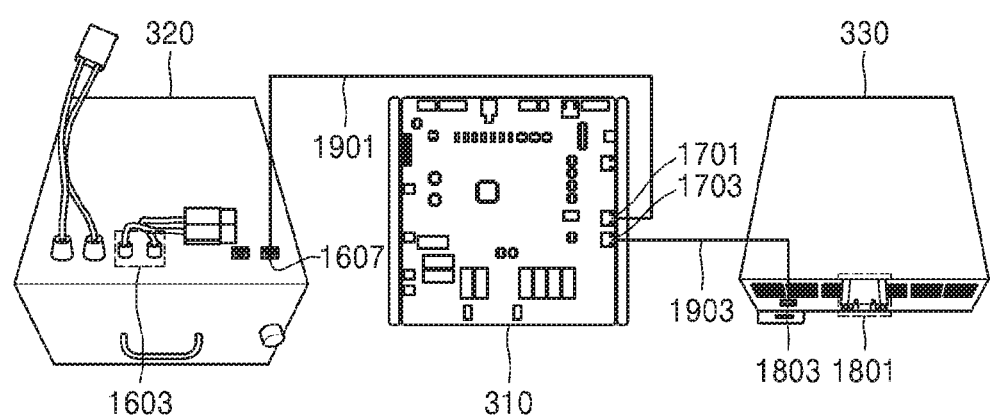
FIG. 19 illustrates a state in which a power supply, a controller, and a charger are connected to one another, according to an embodiment.

FIG. 19 illustrates a state in which a power supply 320, a controller 310, and a charger 330 are connected to one another, according to an embodiment.

Referring to FIG. 19, an X-ray apparatus may include the power supply 320, the controller 310, and the charger 330.

A charging terminal 1603 of the power supply 320 is connected to a charging power supply terminal 1801 of the charger 330 via a cable to receive power necessary to charge a battery cell (not shown) from the charger 330.

The power supply 320, the controller 310, and the charger 330 are electrically connected to one another via communication connectors and cables to perform communications therebetween according to a CAN protocol.

For example, a second communication connector 1607 may be connected to a third communication connector 1701 of the controller 310 via a cable 1901. A fourth communication connector 1703 of the controller 310 may be connected to a fifth communication connector 1803 of the charger 330 via a cable 1903.

The power supply 320, the controller 310, and the charger 330 may transmit or receive data by performing communications therebetween according to the CAN protocol.

The X-ray apparatus may use second through fifth communication connectors 1607, 1710, 1703, and 1803 to update the power supply 320 and the charger 330. When the power supply 320 and the charger 330 are updated via the second through fifth communication connectors 1607, 1710, 1703, and 1803, firmware for the power supply 320 and firmware for the charger 330 may be respectively transmitted to the power supply 320 and the charger 330 via a system board. This eliminates the need for separating the power supply 320 and the charger 330 from the X-ray apparatus.

According to embodiments, the power supply 320, the controller 310, and the charger 330 may be connected using wireless communication.

Figure 20:
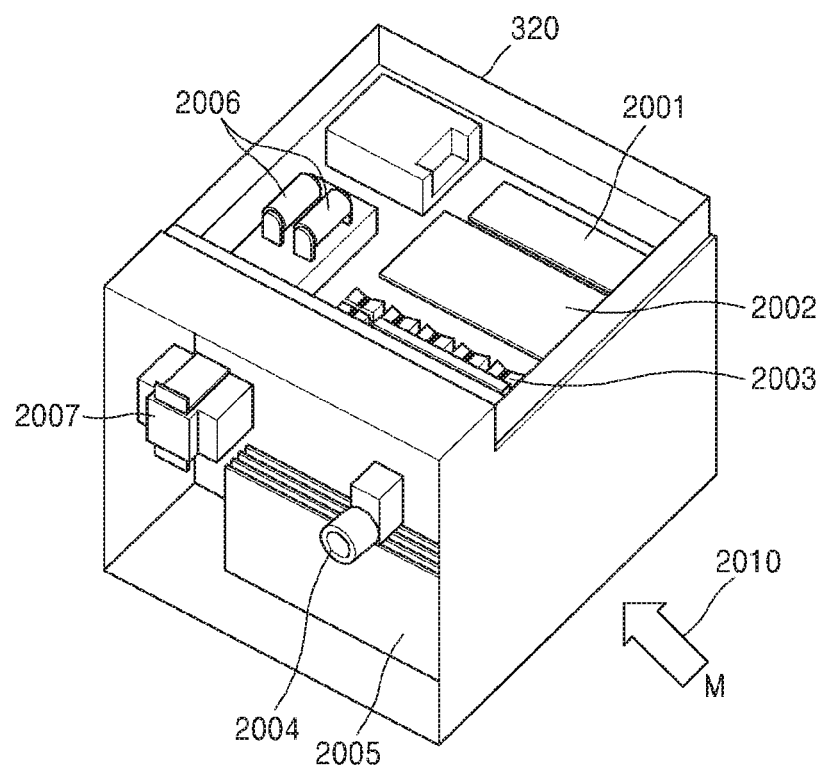
FIG. 20 illustrates a power supply according to an embodiment.

FIG. 20 illustrates an internal structure of a power supply 320 according to an embodiment.

Referring to FIG. 20, the power supply 320 may include a shutdown circuit 2001, a master BMS circuit 2002, an FET 2003, a wake up button 2004, a slave BMS circuit 2005, a fuse 2006, and a BMS switch 2007.

Since the components 2001 through 2006 perform the same functions as their counterparts described with reference to FIGS. 4 through 7, detailed descriptions of the functions will be omitted below.

A structure in which the components are arranged along an M direction 2010 will now be described.

The shutdown circuit 2001 may be positioned in an upper right side of the power supply 320.

The master BMS circuit 2002 may be positioned in an upper middle portion of the power supply 320 and adjacent to the shutdown circuit 2001. Since the shutdown circuit 2001 is located close to the master BMS circuit 2002, a cable connecting the shutdown circuit 2001 to the master BMS circuit 2002 may be shortened, and accordingly radiation noise may be reduced.

The shutdown circuit 2001 and the master BMS circuit 2002 may be arranged parallel to a top surface (not shown) of an external case of the power supply 320. Due to this arrangement, electromagnetic noise radiated from an integrated circuit (IC) of the master BMS circuit 2002 in a vertical direction may be shielded by the top surface of the external case.

The FET 2003 may be arranged on a left side of the master BMS circuit 2002.

The wake up button 2004 is positioned at a front portion of the external case. The wake up button 2004 may be a switch necessary for restarting a system after a BMS is shut down.

The slave BMS circuit 2005 may be positioned in a lower left side of the power supply 320. The slave BMS circuit 2005 may be arranged parallel to a front surface of the external case. A plurality of slave BMS circuits 2005 may be arranged parallel to one another. For example, the slave BMS circuit 2005 may be constituted by eight (8) boards that are arranged parallel to one another.

The BMS switch 2007 may supply or block power to a BMS circuit.

Figure 21:
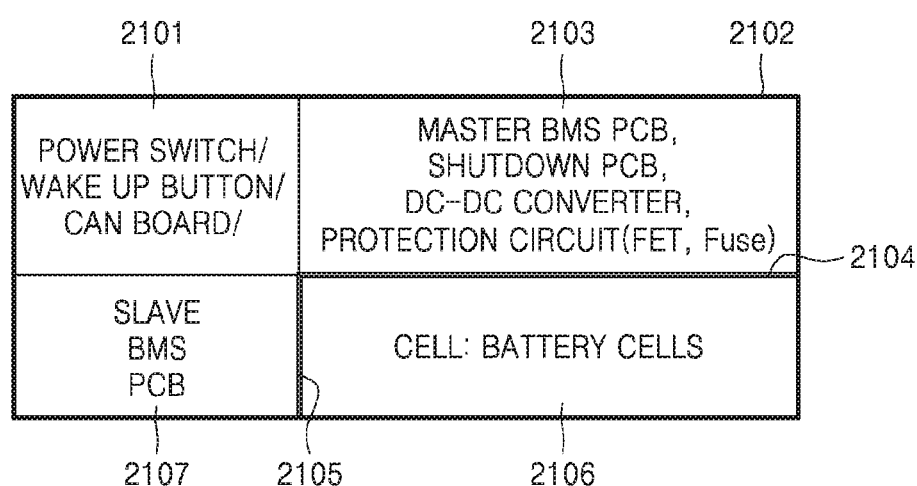
FIG. 21 is a cross-sectional view of a power supply according to an embodiment.

FIG. 21 is a cross-sectional view of a power supply 320 according to an embodiment.

In detail, FIG. 21 shows a cross-section of the power supply 320 taken along the M direction (2010 of FIG. 20).

The power supply 320 may be encased in a metal case 2102.

The power supply 320 may be divided into four (4) regions.

Battery cells 2106 may be arranged in a lower right region of the power supply 320. A structure of the battery cells 2106 will be described in more detail below with reference to FIGS. 23 and 24.

A slave BMS circuit 2107 may be positioned in a lower left region of the power supply 320.

A plurality of circuits 2103, i.e., a master BMS circuit, a shutdown circuit, a DC-DC converter, and a protection circuit (an FET and a fuse) may be arranged in an upper right region of the power supply 320, which is positioned above the battery cells 2106.

A plurality of components 2101, i.e., a power switch, a wake up switch, and a CAN board may be arranged in an upper left region of the power supply 320, which is positioned above the slave BMS circuit 2107.

The battery cells 2106 and the slave BMS circuit 2107 are separated by a partition wall 2105 so that a liquid leaking from the battery cells 2106 may not flow into the slave BMS circuit 2107. The partition wall 2105 may be constituted by a frame made of an insulation material, but is not limited thereto.

The battery cells 2106 and the plurality of circuits 2103 are separated by a partition wall 2104 so that a liquid leaking from the battery cells 2106 may not flow into the plurality of circuits 2103, i.e., the master BMS circuit, the shutdown circuit, the DC-DC converter, and the protection circuit (the FET and the fuse). The partition wall 2104 may be constituted by a frame made of an insulation material, but is not limited thereto.

Figure 22:
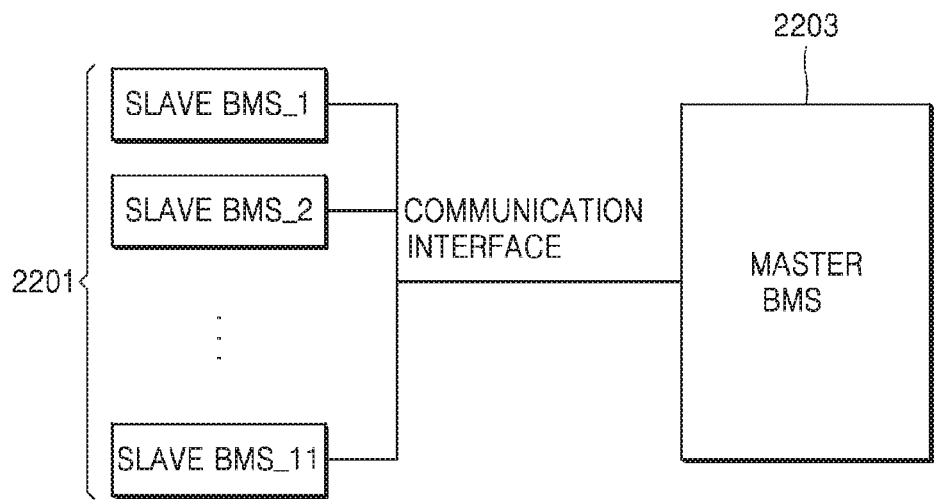
FIG. 22 is a block diagram of a configuration of a battery management system (BMS) circuit according to an embodiment.

FIG. 22 is a block diagram of a configuration of a BMS circuit according to an embodiment.

The BMS circuit may include a slave BMS circuit 2201 and a master BMS circuit 2203.

The slave BMS circuit 2201 may manage voltages, temperatures, and unbalancing between cells of a battery pack with a number of cell groups, e.g., eleven cell groups, connected in series.

For cell balancing, a resistor is used to discharge overcharged cells while charging other cells.

As described above with reference to FIG. 4, four (4) individual battery cells are connected in parallel to form a cell group, and eleven cell groups are connected together in series to form a battery pack.

According to the embodiment, the BMS circuit includes eight (8) slave BMS circuits 2201, but the number of slave BMS circuits 2201 may vary depending on the number of battery packs.

The slave BMS circuit 2201 may include a communication interface and communicate with the master BMS circuit 2203 via the communication interface to transmit voltages, temperatures, and information about unbalancing between cells of a battery pack to the master BMS circuit 2203.

The master BMS circuit 2203 may collect information received from the eight slave BMS circuits 2201 to operate a protection circuit (not shown) and transmit the collected information to a system board via the communication interface (communication connector).

As described above, the slave BMS circuit 2201 manages a voltage and a temperature of battery cells and information about unbalancing between battery cells in a dispersed manner, and the master BMS circuit 2203 collects and manages them in an integrated manner. Due to this configuration, a size of the master BMS circuit 2203 may be reduced. In particular, by dispersedly connecting cables respectively coupled to battery cells to the slave BMS circuit 2201, it is possible to facilitate arrangement of cables and accordingly, improve assembly capabilities. Furthermore, if a problem occurs in the slave BMS circuit 2201, only the faulty slave BMS circuit 2201 may be replaced. Thus, service efficiency may be enhanced.

Figure 23:
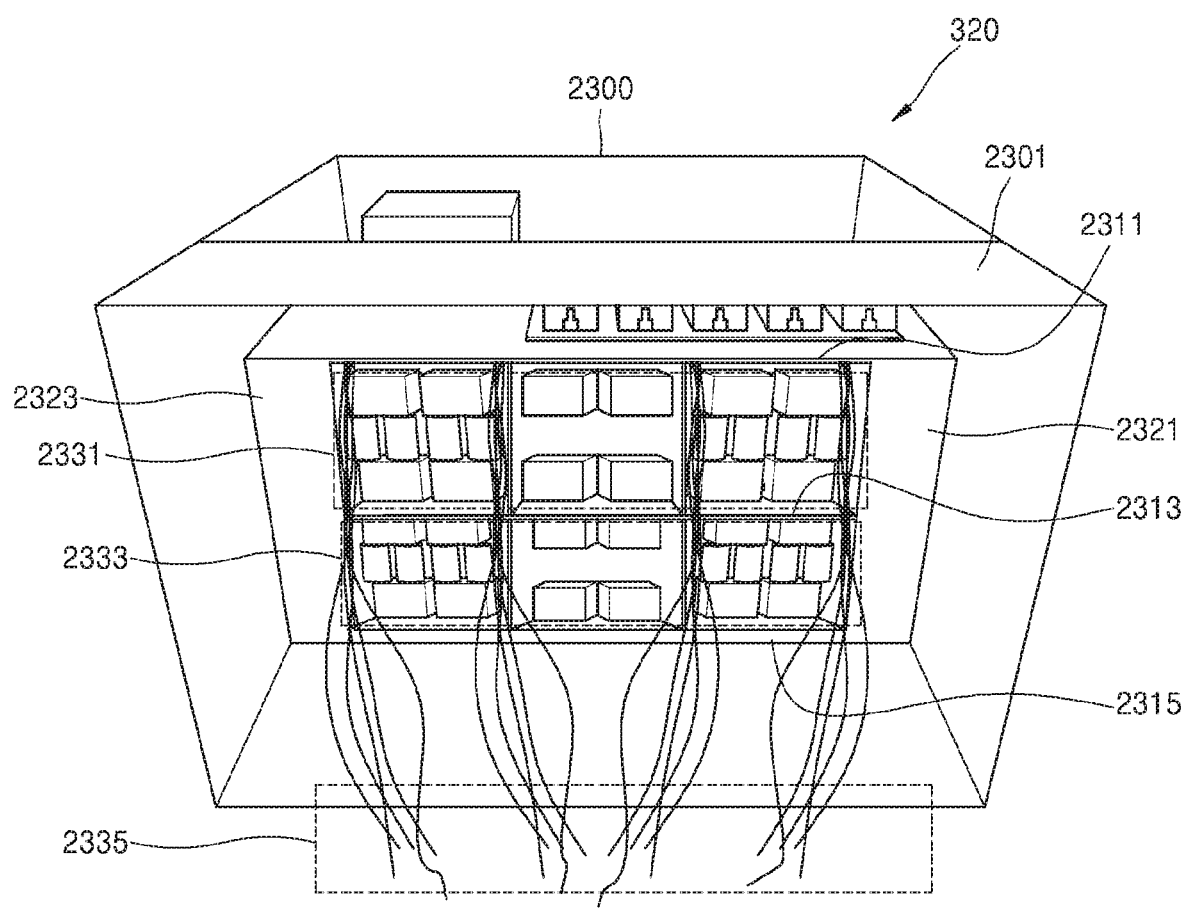
FIG. 23 shows a state in which a battery pack is mounted in a power supply according to an embodiment.

FIG. 23 shows a state in which battery packs are mounted in a power supply 320 according to an embodiment.

Referring to FIG. 23, upper and lower battery packs 2331 and 2333 are mounted in an external case 2300 of the power supply 320.

A reinforcement member 2301 is provided on one side of the external case 2300.

The upper and lower battery packs 2331 and 2333 may be installed in the external case 2300 and stacked in two layers. A plurality of cables 2335 may be connected to the upper and lower battery packs 2331 and 2333 in order to connect the upper and lower battery packs 2331 and 2333 with slave BMS circuits (not shown).

A partition wall 2315 may be installed between the lower battery pack 2333 and a bottom surface of the external case 2300.

A partition wall 2313 may be provided between the upper and lower battery packs 2331 and 2333.

A partition wall 2311 may be provided between the upper battery pack 2331 and a region where a master BMS circuit (not shown) is positioned.

The partition walls 2311 and 2313 may be each formed of an insulation material.

Furthermore, reinforcement members 2321 and 2323 may respectively be provided on right and left sides of the upper and lower battery packs 2331 and 2333. The reinforcement members 2321 and 2323 may protect the upper and lower battery packs 2331 and 2333 by preventing deformation of the external case 2300 caused by an external force.

The external case 2300 may be formed of a thick metal (e.g., with a 1.6t thickness) in order to protect the upper and lower battery packs 2331 and 2333 and other main components of the power supply 320 against an external force.

In addition, for battery cells in a battery pack, lithium ion battery cells are used. Since a battery pack using lithium ion batteries is relatively small and lightweight compared to a battery pack using lead-acid batteries, a slim X-ray apparatus may be provided.

Due to the use of a lithium ion battery, a total weight of the power supply 320 including battery cells and peripheral circuits does not exceed 35 kg, which is the maximum allowable gross weight for carrying on an aircraft. Thus, the power supply 320 may be transported by air as a single component.

Figure 24:
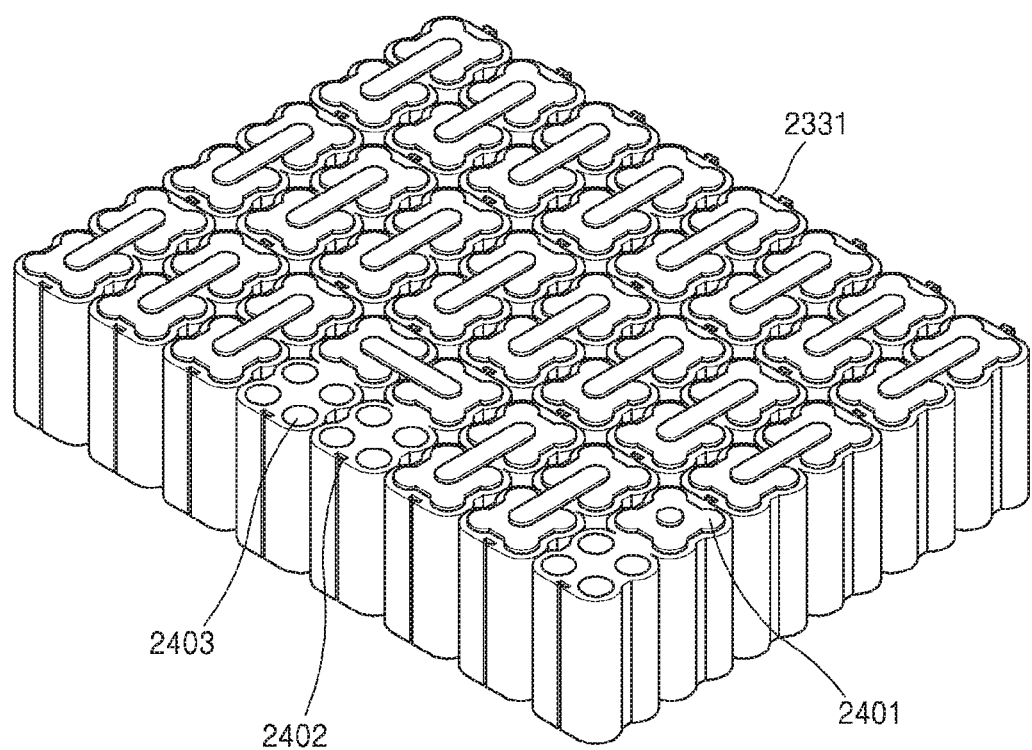
FIG. 24 illustrates a structure of a battery pack according to an embodiment.

FIG. 24 illustrates a structure of a battery pack 2331 according to an embodiment.

Referring to FIG. 24, the battery pack 2331 may include a cell group 2401 and a battery holder 2402.

The cell group 2401 includes four battery cells connected in parallel. In other words, the four battery cells are connected together to form the cell group 2401. Furthermore, eleven cell groups are connected together in series to form the battery pack 2331.

The number of battery cells in a cell group and the number of cell groups in a battery pack are merely an example, and may be adjusted to suit an intended purpose.

The battery holder 2402 may accommodate and protect battery cells. The battery holder 2402 may be made of a flame retardant resin and has holes 2403 formed therein for receiving the battery cells. The battery holder 2402 may also be combined with another battery holder by a pin. Since the battery cells are housed in the battery holder 2402, even when a battery cell gets swollen, the swollen battery cell may not adversely affect another battery cell or component.

Figure 25:
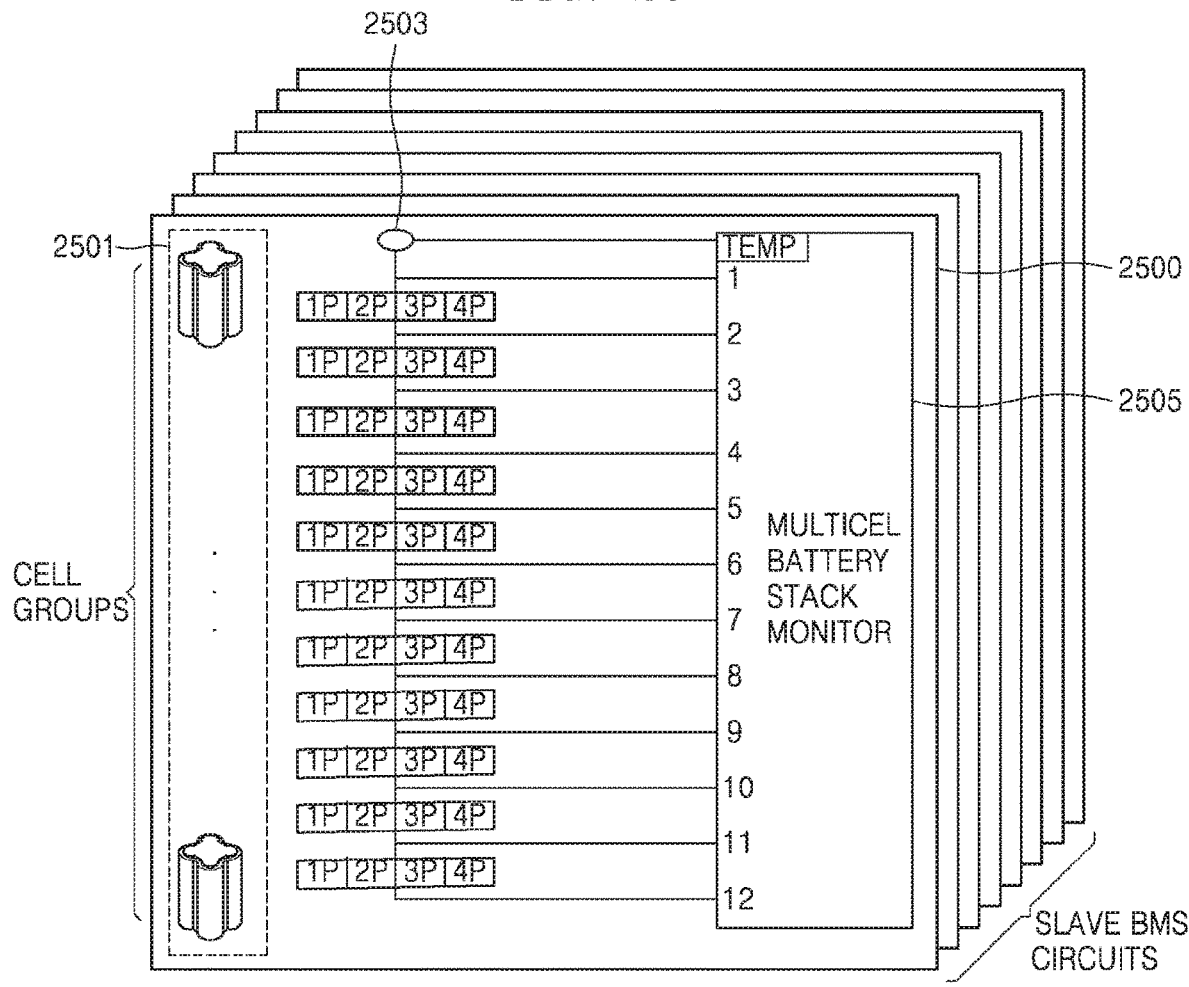
FIG. 25 illustrates a configuration of a slave BMS circuit according to an embodiment.

FIG. 25 illustrates a configuration of a slave BMS circuit 2500 according to an embodiment.

Referring to FIG. 25, the slave BMS circuit 2500 may include a temperature sensor 2503 and a multi-cell battery stack monitor IC 2505.

The temperature sensor 2503 may detect temperatures of a battery cell having eleven cell groups connected in series. In detail, the temperature sensor 2503 may be connected to a top and a bottom of four battery cells 2501 in each cell group to detect a temperature of the battery cells in each cell group.

The temperature sensor 2503 detects temperatures of the 11 cell groups and transmits the result to the multi-cell battery stack monitor IC 2505.

As described above, a BMS circuit includes eight slave BMS circuits 2500, each of which may transmit temperatures, voltages, and information about unbalancing between cells of a battery pack to a master BMS circuit via a communication interface.

Figure 26:
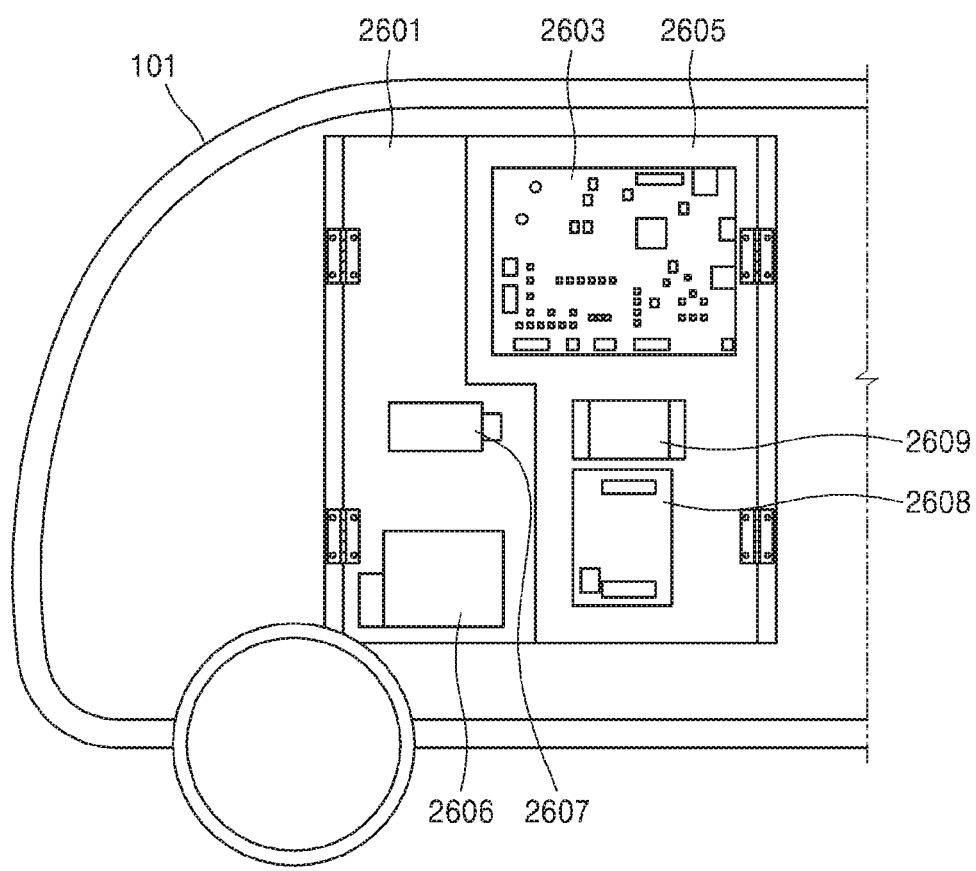
FIG. 26 illustrates a structure in which a system board is mounted on a side of an X-ray apparatus, according to an embodiment.

FIG. 26 illustrates a structure in which a system board 2603 is mounted on a side of an X-ray apparatus, according to an embodiment.

Referring to FIG. 26, frames 2601 and 2605 and the system board 2603 are provided on a side of the X-ray apparatus.

The system board 2603 may be a part of a controller.

The frames 2601 and 2605 may each have one side attached to a main body 101 via a hinge and may be pivoted around a hinge axis.

As the frames 2601 and 2605 are pivoted around the hinge axis, an internal system board mounted in the frames 2601 and 2605 may be exposed to outside the frames 2601 and 2605.

Circuit components 2606, 2607, 2608, and 2609 and the system board 2603 may be mounted on the frames 2601 and 2605.

Figure 27:
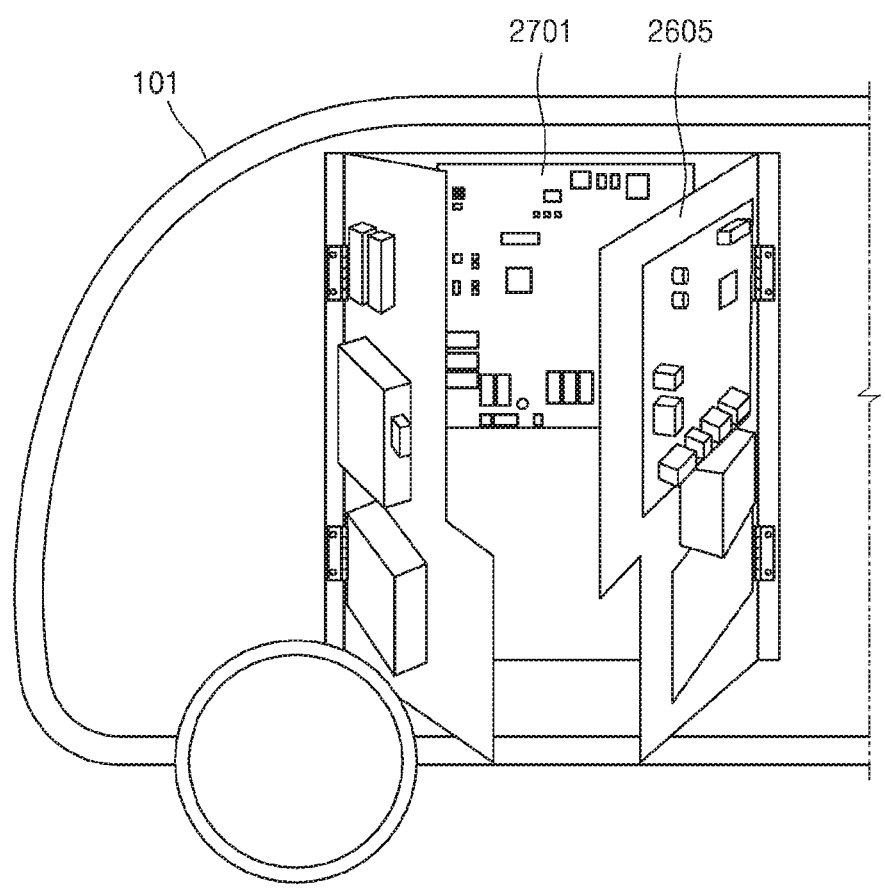
FIG. 27 illustrates a state in which frames of FIG. 26 are open.

FIG. 27 illustrates a state in which the frames 2601 and 2605 of FIG. 26 are open.

FIG. 27 shows the frames 2601 and 2605 and an internal system board 2701.

The frames 2601 and 2605 may be pivoted around a hinge axis to be opened or closed in a transverse direction.

When the frames 2601 and 2605 open, the internal system board 2701 may be exposed to outside. When a problem occurs in the internal system board 2701, the internal system board 2701 may be easily detached from the main body 101 by opening the frames 2601 and 2605 in the transverse direction. Accordingly, service efficiency may be increased.

While one or more embodiments have been described with reference to the figures, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

What is claimed is:

1. A mobile X-ray apparatus comprising:
an X-ray radiation device;
a controller configured to control the X-ray radiation device;
a power supply configured to:
supply operating power to the X-ray radiation device and the controller via a lithium ion battery; and
control an overcurrent that occurs during an X-ray emission by the X-ray radiation device;
a charger configured to charge the lithium ion battery; and
a main body configured to house the controller, the power supply, and the charger,
wherein each of the controller, the power supply, and the charger is embodied as a physically separate module,
wherein the power supply is encased in a metal case,
wherein the power supply includes a master BMS circuit configured to operate a protection circuit against the overcurrent, based on a state of the lithium ion battery, and
wherein the master BMS circuit is arranged parallel to a first surface of the metal case of the power supply.

2. The mobile X-ray apparatus of claim 1, wherein the power supply further includes a shutdown circuit arranged adjacent to the master BMS circuit and parallel to the first surface of the metal case of the power supply.

3. The mobile X-ray apparatus of claim 1, wherein the power supply further includes a slave BMS circuit configured to manage at least one voltage of the lithium ion battery, temperatures of the lithium ion battery, and unbalancing between cells of the lithium ion battery, and
wherein the slave BMS circuit is arranged parallel to a second surface of the metal case that is perpendicular to the first surface.

4. The mobile X-ray apparatus of claim 1, wherein the power supply further includes a slave BMS circuit configured to manage at least one voltage of the lithium ion battery, temperatures of the lithium ion battery, and unbalancing between cells of the lithium ion battery,
wherein the power supply further includes a partition wall including an insulation material, and
wherein the partition wall is installed between the lithium ion battery and the slave BMS circuit.

5. The mobile X-ray apparatus of claim 1, wherein the power supply further includes a partition wall including an insulation material, and
wherein the partition wall is installed between the lithium ion battery and the master BMS circuit.

6. A mobile X-ray apparatus comprising:
an X-ray radiation device;
a controller configured to control the X-ray radiation device;
a power supply configured to:
supply operating power to the X-ray radiation device and the controller via a lithium ion battery; and
control an overcurrent that occurs during an X-ray emission by the X-ray radiation device;
a charger configured to charge the lithium ion battery; and
a main body configured to house the controller, the power supply, and the charger,
wherein each of the controller, the power supply, and the charger is embodied as a physically separate module,
wherein the charger is encased in a metal case,
wherein the power supply includes a master BMS circuit configured to operate a protection circuit against the overcurrent, based on a state of the lithium ion battery, and
wherein the master BMS circuit is arranged parallel to a first surface of the metal case of the power supply.

7. The mobile X-ray apparatus of claim 6, wherein the power supply further includes a shutdown circuit arranged adjacent to the master BMS circuit and parallel to the first surface of the metal case of the power supply.

8. The mobile X-ray apparatus of claim 6, wherein the power supply further includes a slave BMS circuit configured to manage at least one voltage of the lithium ion battery, temperatures of the lithium ion battery, and unbalancing between cells of the lithium ion battery,
wherein the power supply further includes a partition wall including an insulation material, and
wherein the partition wall is installed between the lithium ion battery and the slave BMS circuit.

9. The mobile X-ray apparatus of claim 6, wherein the power supply further includes a partition wall including an insulation material, and
wherein the partition wall is installed between the lithium ion battery and the master BMS circuit.

* * * * *